(12) United States Patent
Sasahara et al.

(10) Patent No.: US 10,113,161 B2
(45) Date of Patent: Oct. 30, 2018

(54) MUTANT GLUTAMATE-CYSTEINE LIGASE AND METHOD FOR MANUFACTURING GAMMA GLUTAMYL-VALYL-GLYCINE

(71) Applicant: AJINOMOTO CO., INC., Tokyo (JP)

(72) Inventors: Ayako Sasahara, Kawasaki (JP); Eri Tabuchi, Kawasaki (JP); Hideyuki Suzuki, Kyoto (JP); Uno Tagami, Kawasaki (JP); Tatsuki Kashiwagi, Kawasaki (JP); Takayuki Ito, Kawasaki (JP); Hiroyuki Nozaki, Kawasaki (JP); Shunichi Suzuki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 54 days.

(21) Appl. No.: 15/223,662

(22) Filed: Jul. 29, 2016

(65) Prior Publication Data

US 2016/0326510 A1   Nov. 10, 2016

Related U.S. Application Data

(63) Continuation of application No. PCT/JP2015/052741, filed on Jan. 30, 2015.

(30) Foreign Application Priority Data

Jan. 31, 2014 (JP) .................. 2014-016601

(51) Int. Cl.
    *C12P 21/02*   (2006.01)
    *C12N 9/00*    (2006.01)
    *C07K 5/02*    (2006.01)

(52) U.S. Cl.
    CPC .............. *C12N 9/93* (2013.01); *C07K 5/0215* (2013.01); *C12P 21/02* (2013.01); *C12Y 603/02002* (2013.01)

(58) Field of Classification Search
    None
    See application file for complete search history.

(56) References Cited

U.S. PATENT DOCUMENTS

| | | |
|---|---|---|
| 2009/0239310 A1 | 9/2009 | Ohsu et al. |
| 2009/0239808 A1 | 9/2009 | Ohsu et al. |
| 2010/0105864 A1 | 4/2010 | Yoneda et al. |
| 2010/0120698 A1 | 5/2010 | Nagasaki et al. |
| 2010/0183792 A1 | 7/2010 | Nagasaki et al. |
| 2010/0203592 A1 | 8/2010 | Tabata et al. |
| 2011/0046046 A1 | 2/2011 | Hara et al. |
| 2011/0071075 A1 | 3/2011 | Takeuchi et al. |
| 2014/0212920 A1 | 7/2014 | Nozaki et al. |

FOREIGN PATENT DOCUMENTS

| | | |
|---|---|---|
| EP | 2251413 A1 | 11/2010 |
| JP | H08-119916 A | 5/1996 |
| JP | 2001-321118 A | 11/2001 |
| JP | 2005-296005 A | 10/2005 |
| JP | 2012-085637 A | 5/2012 |
| WO | WO 2013/054447 A1 | 4/2013 |

OTHER PUBLICATIONS

White et al., Analyt. Biochem. 318:175-180, 2003.*
Chapter 3, "Mutational analysis of S. cerevisiae y-GCS", retrieved from shodhganga.inflibnet.ac.in/bitstream/10603/29825/8/08_chapter%203.pdf on Jan. 24, 2018, 42 pages.*
Partial supplementary European search report dated Jul. 21, 2017 of the corresponding European Patent Application No. 15743180.0.
Lu Feng, et al. "A Recalibrated Molecular Clock and Independent Origins for the Cholera Pandemic Clones", PLOS One, 2008, vol. 3, No. 12, e4053, XP55376318A, pp. 1-11.
Database Uni Prot [Online], Nov. 13, 2013, Database accession No. C3LS46, 2 pages.
XP002770609, Database Uni Prot [Online], Oct. 31, 2006, Database accession No. Q9TY17, 1 page.
XP002770610, Database GeneBank [Online], Nov. 26, 1998, Database accession No. AF095637, 2 pages.
John F. Heldelberg, et al., "DNA sequence of both chromosomes of the cholera pathogen Vibrio cholerae", Nature, 2000, vol. 4 0 6, No. 6795, XP055125439, pp. 477-484.
Database GenBank [Online], Jan. 31, 2014, Database accession No. AAF93724, 3 pages.
C. K. Stover, et al., "Complete genome sequence of Pseudomonas aeruginosa PA01, an opportunistic pathogen", Nature, 2000, vol. 406, No. 6799, XP055125439, pp. 959-964.
Database NCBI [Online], Apr. 26, 2009, Database accession No. NP253890, 3 pages.
Roeland C. H. J. Van Ham, et al., "Reductive genome evolution in *Buchnera aphidicola*", PNAS, 2003, vol. 100, No. 2, XP55184259, pp. 581-586.
Database Protein [Online], Dec. 17, 2014, Database accession No. NP777980, 5 pages.
L. L. Reid, et al "Molecular cloning and sequencing of the cDNA encoding mouse glutamate-cysteine ligase regulatory subunit", Biochimica Et Biophysica ACTA, 1997, vol. 1353, X002770612, pp. 107-110.
Database GenBank [Online], Jan. 17, 1998, Database accession No. U95053, 2 pages.
Hideyuki Suzuki, et al., "Enzymatic Synthesis of y-Glutamylvaline to Improve the Bitter Taste of Valine", Journal of Agricultural and Food Chemistry, 2004, vol. 52, XP002735891, pp. 577-580.
International Search Report dated Apr. 21, 2015, in PCT/JP2015/052741 (filed Jan. 30, 2015).

(Continued)

*Primary Examiner* — David Steadman
(74) *Attorney, Agent, or Firm* — Oblon, McClelland, Maier & Neustadt, L.L.P.

(57) ABSTRACT

A mutant glutamate-cysteine ligase (GSHA) suitable for generating γ-Glu-Val, and a method for producing γ-Glu-Val-Gly using the same are provided. γ-Glu-Val is produced by using a mutant GSHA having a specific mutation with Glu and Val as raw materials, and γ-Glu-Val-Gly is further produced by using γ-Glu-Val and Gly as raw materials. γ-Glu-Val-Gly is produced by using a mutant GSHA having a specific mutation with Glu, Val, and Gly as raw materials.

23 Claims, No Drawings
Specification includes a Sequence Listing.

(56) References Cited

OTHER PUBLICATIONS

Kelly B.S. et al., *Escherichia coil* gamma-glutamylcysteine synthetase, two active site metal ions affect substrate and inhibitor binding., The Journal of Biological Chemistry, 2002, vol. 277, No. 1, pp. 50-58.
Kumagai H. et al., γ-Glutamylcysteine Synthetase from Proteus mirabilis., Agric. Biol. Chem., 1982, vol. 46, No. 5, pp. 1301-1309.
Notification of Transmittal of Translation of the International Preliminary Report on Patentability (11 pages) Aug. 11 , 2016.

* cited by examiner

MUTANT GLUTAMATE-CYSTEINE LIGASE AND METHOD FOR MANUFACTURING GAMMA GLUTAMYL-VALYL-GLYCINE

TECHNICAL FIELD

The present invention relates to a method for producing γ-glutamylvalylglycine, and a mutant of glutamate-cysteine ligase which can be preferably used for the method. γ-Glutamylvalylglycine is useful in the fields of food, drug, and so forth.

BACKGROUND ART

Certain kinds of peptides such as γ-glutamylvalylglycine (L-γ-glutamyl-L-valyl-glycine, henceforth also referred to as "γ-Glu-Val-Gly") have a calcium sensing receptor agonist activity (Patent document 1). Such peptides having a calcium receptor agonist activity are known to be able to impart "kokumi" to foods and drinks (Patent document 2), improve tastes of low fat foods, especially fat-like thickness and smoothness (Patent document 3), improve feeling of body of sweet taste substances, and improve bitterness peculiar to sweet taste substances (Patent document 4).

Moreover, such peptides as mentioned above are known to have a prophylactic or curative effect on diarrhea (Patent document 5) and diabetes (Patent document 6), and a bicarbonate secretion promoting effect in the alimentary tract (Patent document 7).

As methods for producing γ-glutamyl tripeptides, chemical synthesis methods and enzymatic methods are generally known. As one of the chemical synthesis methods, a method of selectively obtaining a γ-glutamyl tripeptide from a dipeptide by using N-protected glutamic anhydride is known (Patent document 8). As one of the enzymatic methods, there is known a method of using glutamate-cysteine ligase and glutathione synthetase is known (Patent documents 9 and 10). As another enzymatic method, there is also known a method of γ-glutamylating Val-Gly by using γ-glutamyltransferase to generate γ-Glu-Val-Gly (Patent document 11).

Glutamate-cysteine ligase (GSHA) is an enzyme having an activity for catalyzing the reaction of generating γ-Glu-Cys, ADP, and phosphate using Glu, Cys, and ATP as substrates (EC 6.3.2.2). GSHA usually requires divalent metal ions such as $Mg^{2+}$ and $Mn^{2+}$ for the enzymatic reaction.

GSHA of *Escherichia coli* generates γ-glutamyl peptides using Glu, various kinds of amino acids, and ATP as substrates in the presence of $Mg^{2+}$ or $Mn^{2+}$, and it is known that type of the metal ion serving as a cofactor affects the substrate specificity thereof (Non-patent document 1). Specifically, it has been reported that when $Mg^{2+}$ is used as the cofactor, Vmax is 251 mol/mg/hr and Km is 17.6 mM as for the γ-Glu-Gly generation activity, whereas Vmax is 59 mol/mg/hr and Km is 27.1 mM as for the γ-Glu-Val generation activity. That is, if the activities are compared by using Vmax/Km as index of the activities, the ratio of γ-Glu-Val generation activity to the γ-Glu-Gly generation activity in the case of using $Mg^{2+}$ as the cofactor can be calculated to be 0.15. Further, it has been demonstrated that when $Mn^{2+}$ is used as the cofactor, Vmax is 39 mol/mg/hr and Km is 1.7 mM as for the γ-Glu-Gly generation activity, whereas Vmax is 95 mol/mg/hr and Km is 21 mM as for the γ-Glu-Val generation activity. That is, if the activities are compared by using Vmax/Km as index of the activities, the ratio of γ-Glu-Val generation activity to the γ-Glu-Gly generation activity in the case of using $Mn^{2+}$ as the cofactor can be calculated to be 0.20.

It is also known that GSHA derived from *Proteus mirabilis*, a kind of gram-negative bacteria, generates γ-glutamyl peptides by using $Mg^{2+}$ or $Mn^{2+}$ as a cofactor, as well as Glu, various kinds of amino acids, and ATP as substrates (Non-patent document 2). It has been reported that if the γ-Glu-Cys generation activity of GSHA derived from *Proteus mirabilis* is taken as 100%, the γ-Glu-Gly generation activity and γ-Glu-Val generation activity of the same correspond to 14.5% and 7.2%, respectively. That is, if the activities are compared on the basis of these relative activities, the ratio of γ-Glu-Val generation activity to the γ-Glu-Gly generation activity can be calculated to be 0.50.

PRIOR ART REFERENCES

Patent Documents

Patent document 1: WO2007/055388
Patent document 2: WO2007/055393
Patent document 3: WO2008/139945
Patent document 4: WO2008/139946
Patent document 5: WO2008/139947
Patent document 6: WO2009/107660
Patent document 7: WO2009/119554
Patent document 8: Japanese Patent Laid-open (Kokai) No. 08-119916
Patent document 9: WO2013/054447
Patent document 10: Japanese Patent Laid-open (Kokai) No. 2012-85637
Patent document 11: WO2013/051685

Non-Patent Documents

Non-patent document 1: Brenda S. Kelly et al., J. Biol. Chem., 277, 50-58, 2002
Non-patent document 2: Kumagai, H. et al., Agric. Biol. Chem., 46, 1301-1309, 1982

SUMMARY OF THE INVENTION

Object to be Achieved by the Invention

Glutamate-cysteine ligase (GSHA) plays a role of generating γ-Glu-Cys, which is a precursor of glutathione, in vivo. Although GSHA can use various amino acids as a substrate besides Cys, the activity for using Val, which is a kind of branched chain amino acid, as a substrate is relatively low compared with that for using Cys. Therefore, when γ-Glu-Val-Gly is produced by using GSHA and glutathione synthetase with Glu, Val, and Gly as raw materials, there arises a problem that the yield of γ-Glu-Val-Gly is low. Therefore, an object of the present invention is to provide a mutant of GSHA suitable for generating γ-Glu-Val, and a method for producing γ-Glu-Val-Gly using it.

Means for Achieving the Object

The inventors of the present invention conducted various researches in order to achieve the aforementioned object, as a result, found mutations of GSHA that improve the ratio of the activity for generating γ-Glu-Val to the activity for generating γ-Glu-Gly, and accomplished the present invention.

Thus, the present invention can be embodied, for example, as follows.

[1]

A mutant glutamate-cysteine ligase having a mutation for an amino acid residue or amino acid residues corresponding to one or more amino acid residues selected from those mentioned below in a wild-type glutamate-cysteine ligase, and having the γ-glutamylvaline synthetase activity:
L135, Q144, Y241, N243, Y300.

[2]

The mutant glutamate-cysteine ligase mentioned above, wherein the mutation includes a mutation corresponding to one or more mutations selected from those mentioned below:
L135 (I, F, M, V, G, A, W, K, H, R, C, N, S, T),
Q144 (F, A, N, S, D, T, R, H, G, K, Y, W, C, M, P, V, L, I),
Y241 (A),
N243 (I, W, K, R, H),
Y300 (A, H, R, K).

[3]

The mutant glutamate-cysteine ligase mentioned above, wherein the mutation includes a mutation corresponding to any one of the following mutations:
L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144R/N243F, Q144D/N243W, Q144D/N243F, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, L135T/Q144L.

[4]

The mutant glutamate-cysteine ligase mentioned above, wherein the mutation includes a mutation corresponding to any one of the following mutations:
L135 (I, M, V, G, A, K, H, C, N, S, T),
Q144 (F, A, S, D, I, R, H, K, Y, W, C, M, P, V, L, I),
N243 (R, H),
Y300 (R, K),
L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144P, L135V/Q144W, L135V/Q144H, L135V/Q144E, L135V/Q144N, L135V/Q144S, L135D/Q144L, L135C/Q144L, L135N/Q144L, L135S/Q144L, L135T/Q144L.

[5]

The mutant glutamate-cysteine ligase mentioned above, wherein the wild-type glutamate-cysteine ligase is a protein defined in (a), (b), or (c) mentioned below:
(a) a protein comprising the amino acid sequence of SEQ ID NO: 2;
(b) a protein comprising the amino acid sequence of SEQ ID NO: 2 but including substitution, deletion, insertion, or addition of 1 to 10 amino acid residues;
(c) a protein comprising an amino acid sequence showing an identity of 90% or higher to the amino acid sequence of SEQ ID NO: 2.

The mutant glutamate-cysteine ligase mentioned above, which shows a ratio of γ-glutamylvaline synthetase activity to γ-glutamylglycine synthetase activity of 0.7 or higher.

[7]

A mutant glutamate-cysteine ligase, which shows a ratio of γ-glutamylvaline synthetase activity to γ-glutamylglycine synthetase activity of 0.7 or higher.

[8]

A method for producing γ-Glu-Val and/or a salt thereof, the method comprising the following step (A):
(A) a step of allowing the mutant glutamate-cysteine ligase mentioned above to act on Glu and Val to generate γ-Glu-Val.

[9]

A method for producing γ-Glu-Val-Gly and/or a salt thereof, the method comprising the following steps (A) and (B):
(A) a step of allowing the mutant glutamate-cysteine ligase mentioned above to act on Glu and Val to generate γ-Glu-Val; and
(B) a step of allowing glutathione synthetase to act on γ-Glu-Val generated in the step (A) and Gly to generate γ-Glu-Val-Gly.

[10]

A method for producing γ-Glu-Val-Gly and/or a salt thereof, the method comprising the following step (C):
(C) a step of allowing the mutant glutamate-cysteine ligase mentioned above and glutathione synthetase to act on Glu, Val, and Gly to generate γ-Glu-Val-Gly.

[11]

The method mentioned above, wherein the mutant glutamate-cysteine ligase is a purified enzyme.

[12]

The method mentioned above, wherein the mutant glutamate-cysteine ligase is an immobilized enzyme.

[13]

The method mentioned above, wherein the mutant glutamate-cysteine ligase is an enzyme contained in a culture broth of a microorganism having the enzyme, cultured cells of the microorganism, or a processed product of the cells.

[14]

The method mentioned above, wherein the glutathione synthetase is an enzyme contained in a culture broth of a microorganism having the enzyme, cultured cells of the microorganism, or a processed product of the cells.

[15]

The method mentioned above, wherein the mutant glutamate-cysteine ligase and glutathione synthetase are enzymes contained in a culture broth of a microorganism having both enzymes, cultured cells of the microorganism, or a processed product of the cells.

[16]
The method mentioned above, wherein the microorganism has been modified so that the activity of γ-glutamyltransferase is reduced.
[17]
The method mentioned above, wherein the microorganism is *Escherichia coli*.
[18]
The method mentioned above, wherein the step or steps is/are carried out in the presence of ATP.
[19]
A gene encoding the mutant glutamate-cysteine ligase mentioned above.
[20]
A vector carrying the gene mentioned above.
[21]
A microorganism having the gene or vector mentioned above.
[22]
The microorganism mentioned above, which has been modified so that the activity of γ-glutamyltransferase is reduced.
[23]
The microorganism mentioned above, which has a gene encoding glutathione synthetase.
[24]
The microorganism mentioned above, which is *Escherichia coli*.

MODES FOR CARRYING OUT THE INVENTION

Hereafter, the present invention will be explained in detail. In this description, amino acids are L-amino acids, unless especially indicated.
<1> Mutant Glutamate-cysteine Ligase (Mutant GSHA)
"Glutamate-cysteine ligase" is generally known as an enzyme having an activity for catalyzing the reaction of generating γ-Glu-Cys, ADP, and phosphate using Glu, Cys, and ATP as substrates (EC 6.3.2.2). In the present invention, this activity is also referred to as "γ-glutamylcysteine synthetase activity". In the present invention, glutamate-cysteine ligase is also referred to as "GSHA".
In the present invention, the activity for catalyzing the reaction of generating γ-Glu-Val, ADP, and phosphate by using Glu, Val, and ATP as substrates is also referred to as "γ-glutamylvaline synthetase activity" or "γ-Glu-Val generation activity".
In the present invention, the activity for catalyzing the reaction of generating γ-Glu-Gly, ADP, and phosphate by using Glu, Gly, and ATP as substrates is also referred to as "γ-glutamylglycine synthetase activity" or "γ-Glu-Gly generation activity".
In the present invention, the "mutant glutamate-cysteine ligase (mutant GSHA)" refers to GSHA having a "specific mutation". In the present invention, a gene encoding a mutant GSHA is also referred to as "mutant glutamate-cysteine ligase gene (mutant gshA gene)". The "specific mutation" will be described later.
In the present invention, a glutamate-cysteine ligase not having the "specific mutation" is also referred to as "wild-type glutamate-cysteine ligase (wild-type GSHA)". In the present invention, a gene encoding a wild-type GSHA is also referred to as "wild-type glutamate-cysteine ligase gene (wild-type gshA gene)". The term "wild-type" used here is a term used for convenience for indicating that a gene or enzyme is not "mutant", and the wild-type gene or enzyme is not limited to a naturally occurring one, so long as the gene or enzyme does not have the "specific mutation".

Hereafter, the wild-type GSHA will be explained. Examples of the wild-type GSHA include the GshA protein encoded by the gshA gene of *Escherichia coli* (GSHA of *Escherichia coli*). The nucleotide sequence of the gshA gene of the *Escherichia coli* K-12 MG1655 strain is disclosed in Blattner F R, et al., Science, 277:1453-62 (1997), and corresponds to the complementary sequence of the sequence of the positions 2,814,883 to 2,816,439 in the genome sequence registered at the NCBI database as GenBank accession NC_000913.3. The nucleotide sequence of the gshA gene of the MG1655 strain is shown as SEQ ID NO: 1. The amino acid sequence of the protein encoded by this gene is shown as SEQ ID NO: 2. That is, the wild-type GSHA may be, for example, a protein encoded by a gene having the nucleotide sequence shown as SEQ ID NO: 1. The wild-type GSHA may also be, for example, a protein having the amino acid sequence shown as SEQ ID NO: 2. The expression of "having an (amino acid or nucleotide) sequence" includes both cases of "containing the (amino acid or nucleotide) sequence" and "consisting of the (amino acid or nucleotide) sequence".

The wild-type GSHA may be a variant of the wild-type GSHA exemplified above (GSHA of *Escherichia coli* such as a protein having the amino acid sequence shown as SEQ ID NO: 2), so long as it does not have the "specific mutation". That is, the wild-type GSHA may have another mutation, so long as it does not have the "specific mutation". Examples of the variant include, for example, a homologue of the wild-type GSHA exemplified above and an artificially modified version of the wild-type GSHA exemplified above. Examples of the homologue of GSHA of *Escherichia coli* include GSHA homologues of other microorganisms, of which structure is similar to that of GSHA of *Escherichia coli*. Examples of the GSHA homologues of other microorganisms include GSHA homologues of bacteria belonging to the family Enterobacteriaceae such as other *Escherichia* bacteria, *Enterobacter* bacteria, and *Pantoea* bacteria. GSHA homologues of other microorganisms can be obtained from, for example, a public database by BLAST search and FASTA search using the amino acid sequence of the wild-type GSHA exemplified above as a query sequence.

The wild-type GSHA may typically be a protein having the γ-glutamylcysteine synthetase activity. However, in the present invention, so long as the corresponding mutant GSHA has the γ-glutamylvaline synthetase activity, the wild-type GSHA may have the γ-glutamylcysteine synthetase activity, γ-glutamylvaline synthetase activity, γ-glutamylglycine synthetase activity, or an arbitrary combination of these, or may not have any of these activities.

The wild-type GSHA may be a protein having an amino acid sequence corresponding to the amino acid sequence of the aforementioned wild-type GSHA (for example, SEQ ID NO: 2), but including substitution, deletion, insertion, or addition of one or several amino acid residues at one or several positions, so long as it does not have the "specific mutation". Although the number meant by the term "one or several" can differ depending on the positions of amino acid residues in the three-dimensional structure of the protein, or the types of amino acid residues, specifically, it is preferably 1 to 20, more preferably 1 to 10, still more preferably 1 to 5, particularly preferably 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gin for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation (mutant or variant), such as those due to a difference of individuals or species of the organism from which the gene is derived.

The wild-type GSHA may be a protein showing a homology of 80% or higher, preferably 90% or higher, more preferably 95% or higher, still more preferably 97% or higher, particularly preferably 99% or higher, to the amino acid sequence of the aforementioned wild-type GSHA (for example, SEQ ID NO: 2), so long as it does not have the "specific mutation". In this description, "homology" can mean "identity".

The wild-type GSHA may be a protein encoded by a DNA that is able to hybridize under stringent conditions with a probe that can be prepared from the aforementioned wild-type gshA gene (for example, SEQ ID NO: 1), such as a probe having a sequence complementary to a part or the whole of the nucleotide sequence of the aforementioned wild-type gshA gene (for example, SEQ ID NO: 1), so long as it does not have the "specific mutation". Such a probe can be prepared by PCR using oligonucleotides produced on the basis of a known wild-type gshA gene sequence as primers, and a DNA fragment containing the nucleotide sequence of the wild-type gshA gene as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C. Further, for example, when a DNA fragment having a length of about 300 bp is used as the probe, the washing conditions of the hybridization can be, for example, 50° C., 2×SSC, and 0.1% SDS. Those skilled in the art can realize stringency equivalent to the stringency of the hybridization exemplified above by determining various conditions such as salt concentrations and temperature.

Further, in the wild-type gshA gene, arbitrary codons may be replaced with equivalent codons, so long as it encodes a wild-type GSHA. For example, in the wild-type gshA gene, codons may be optimized according to codon frequencies observed in the host to be used. Specifically, for example, when the start codon is not ATG, the start codon can be modified to ATG.

Hereafter, the mutant GSHA will be explained.

The mutant GSHA has the γ-glutamylvaline synthetase activity.

So long as the mutant GSHA has the γ-glutamylvaline synthetase activity, it may or may not have an activity for generating a γ-glutamyl dipeptide other than γ-glutamylvaline. That is, for example, the mutant GSHA may or may not have the γ-glutamylcysteine synthetase activity. Further, for example, the mutant GSHA may or may not have the γ-glutamylglycine synthetase activity. It is preferred that the mutant GSHA does not have the γ-glutamylglycine synthetase activity.

The mutant GSHA has the "specific mutation" explained later in the amino acid sequence of the wild-type GSHA.

That is, for example, the mutant GSHA may be a protein having the amino acid sequence shown as SEQ ID NO: 2, but including the "specific mutation". The mutant GSHA may also be, for example, a protein having the amino acid sequence shown as SEQ ID NO: 2, but including the "specific mutation", further including substitution, deletion, insertion, or addition of one or several amino acid residues at a site other than that of the "specific mutation", and having the γ-glutamylvaline synthetase activity.

In other words, the mutant GSHA may be a protein having an amino acid sequence identical to that of the wild-type GSHA, except that it has the "specific mutation". For example, the mutant GSHA may be a protein having the amino acid sequence shown as SEQ ID NO: 2, except that it has the "specific mutation". The mutant GSHA may also be, for example, a protein having the amino acid sequence shown as SEQ ID NO: 2, but including substitution, deletion, insertion, or addition of one or several amino acid residues, and having the γ-glutamylvaline synthetase activity, except that it has the "specific mutation". The mutant GSHA may also be, for example, a protein having an amino acid sequence showing a homology of 80% or higher, preferably 90% or higher, more preferably 95% or higher, still more preferably 97% or higher, particularly preferably 99% or higher, to the amino acid sequence shown as SEQ ID NO: 2, and having the γ-glutamylvaline synthetase activity, except that it has the "specific mutation".

The mutant GSHA may be a fusion protein with another peptide. The "another peptide" is not particularly limited so long as the mutant GSHA has the γ-glutamylvaline synthetase activity. The "another peptide" can be selected as required depending on various conditions such as purpose of use thereof. Examples of the "another peptide" include a peptide tag, signal peptide, and recognition sequence of a protease. The "another peptide" may be bound to, for example, either one or both of the N-terminus and C-terminus of the mutant GSHA. As the "another peptide", one kind of peptide may be used, or two or more kinds of peptides may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. Examples of the His tag include 6×His tag. A peptide tag can be utilized for, for example, detection and purification of the expressed mutant GSHA.

The signal peptide is not particularly limited, so long as it functions in a host in which the mutant GSHA is expressed. Examples of the signal peptide include a signal peptide that is recognized by the Sec system secretory pathway and a signal peptide recognized by the Tat system secretory pathway. Specific examples of the signal peptide that is recognized by the Tat system secretory pathway include the TorA signal sequence of *E. coli*, the SufI signal sequence of *E. coli*, the PhoD signal sequence of *Bacillus subtilis*, the LipA signal sequence of *Bacillus subtilis*, and the IMD signal sequence of *Arthrobacter globiformis* (WO2013/118544). A signal peptide can be used for, for example, secretory production of the mutant GSHA. If secretory production of the mutant GSHA is performed by using a signal peptide, the signal peptide may be cleaved at the time of the secretion, and the mutant GSHA not having the signal peptide may be secreted out of the cell.

Specific examples of the recognition sequence of a protease include the recognition sequence of the Factor Xa protease and the recognition sequence of the proTEV protease. The recognition sequence of a protease can be used for, for example, cleavage of the expressed mutant GSHA. Specifically, for example, when the mutant GSHA is expressed as a fusion protein with a peptide tag, if a recognition sequence of a protease is introduced into the connection part of the mutant GSHA and the peptide tag, the peptide tag can be cleaved from the expressed mutant GSHA by using a protease to obtain the mutant GSHA not having the peptide tag.

The mutant GSHA gene is not particularly limited so long as it encodes such a mutant GSHA as mentioned above. In the present invention, a "gene" is not limited to DNA, but may include an arbitrary polynucleotide, so long as it encodes a target protein. That is, the "mutant GSHA gene" may mean an arbitrary polynucleotide encoding a mutant GSHA. The mutant GSHA gene may be DNA, RNA, or a combination thereof. The mutant GSHA gene may be single-stranded or double-stranded. The γ-glutamylvaline synthetase gene may be a single-stranded DNA or a single-stranded RNA. The mutant GSHA gene may be a double-stranded DNA, a double-stranded RNA, or a hybrid strand consisting of a DNA strand and an RNA strand. The mutant GSHA gene may contain both a DNA residue and an RNA residue in a single polynucleotide chain. When the mutant GSHA gene contains RNA, the aforementioned descriptions concerning DNA, such as those concerning nucleotide sequences exemplified above, may be applied to RNA with appropriately changing wordings to those for RNA as required. The mode of the mutant GSHA gene can be chosen according to various conditions such as use thereof.

Hereafter, the "specific mutation" will be explained.

The "specific mutation" refers to a mutation that imparts a characteristic suitable for generation of γ-glutamylvaline to a wild-type GSHA, when it is introduced into the wild-type GSHA. That is, because of having the "specific mutation", the mutant GSHA has a characteristic suitable for generation of γ-glutamylvaline, compared with the wild-type GSHA. Examples of the characteristic suitable for generation of γ-glutamylvaline include, for example, increased γ-glutamylvaline synthetase activity (specific activity), reduced γ-glutamylglycine synthetase activity (specific activity), increased ratio of γ-glutamylvaline synthetase activity (specific activity) to γ-glutamylglycine synthetase activity (specific activity), and a combination thereof.

When γ-glutamylvalylglycine is produced in a single reaction system by using GSHA and glutathione synthetase with Glu, Val, and Gly as the raw materials, γ-glutamylvalylglycine is generated via γ-glutamylvaline as an intermediate. If γ-glutamylglycine is by-produced in this process, the yield of the target γ-glutamylvalylglycine is reduced. Therefore, it is expected that, if, in particular, a mutant GSHA showing an improved ratio of γ-glutamylvaline synthetase activity to γ-glutamylglycine synthetase activity is created, and used for production of γ-glutamylvalylglycine, the yield of γ-glutamylvalylglycine generated via γ-glutamylvaline as an intermediate is improved. In addition, it is also expected that generation of γ-glutamylglycine as a by-product, and generation of other compounds generated via γ-glutamylglycine can be reduced.

The ratio of γ-glutamylvaline synthetase activity (specific activity) to γ-glutamylglycine synthetase activity (specific activity) of the mutant GSHA may be, for example, 0.1 or higher, 0.2 or higher, 0.5 or higher, 0.7 or higher, 1.0 or higher, 5.0 or higher, 10 or higher, or 20 or higher. The ratio of γ-glutamylvaline synthetase activity (specific activity) to γ-glutamylglycine synthetase activity (specific activity) of the mutant GSHA may also be, for example, 10,000,000 or lower, 1,000,000 or lower, 100,000 or lower, 10,000 or lower, 1,000 or lower, or 100 or lower. The ratio of the specific activities can be calculated by measuring the γ-glutamylvaline synthetase activity and γ-glutamylglycine synthetase activity under the conditions described in Example 7. Specific conditions for measurement of the activities are as follows. The γ-glutamylvaline synthetase activity of the mutant GSHA can be measured by, for example, using an appropriate amount of the mutant GSHA with a reaction mixture composition of 10 mM Glu, 10 mM Val, 10 mM ATP, 10 mM $MgSO_4$, 100 mM Tris-HCl buffer (pH 9.0), reaction temperature of 30° C., and reaction time of 1 to 30 minutes. The enzymatic activity for generating 1 μmol of γ-Glu-Val in 1 minute under the aforementioned conditions is defined as 1 U of the γ-glutamylvaline synthetase activity. Similarly, the γ-glutamylglycine synthetase activity of the mutant GSHA can be measured by, for example, using an appropriate amount of the mutant GSHA with a reaction mixture composition of 10 mM Glu, 10 mM Gly, 10 mM ATP, 10 mM $MgSO_4$, 100 mM Tris-HCl buffer (pH 9.0), reaction temperature of 30° C., and reaction time of 1 to 30 minutes. The enzymatic activity for generating 1 μmol of γ-Glu-Gly in 1 minute under the aforementioned conditions is defined as 1 U of the γ-glutamylglycine synthetase activity.

Also, in particular, it is expected that if a mutant GSHA showing an increased γ-glutamylvaline synthetase activity (specific activity) is used, production of γ-glutamylvaline using Glu and Val as raw materials is improved. The γ-glutamylvaline synthetase activity (specific activity) of the mutant GSHA may be increased 1.1 times or more, 1.5 times or more, 2 times or more, 5 times or more, 10 times or more, or 20 times or more, as compared with the wild-type GSHA. The γ-glutamylvaline synthetase activity (specific activity) can be measured by the aforementioned method.

Examples of the "specific mutation" include a mutation corresponding to a mutation at one or more amino acid residues selected from the followings:
L135, Q144, Y241, N243, Y300.

In the aforementioned description, the numerals indicate the positions in the amino acid sequence of the wild-type GSHA shown as SEQ ID NO: 2, and the letters on the left side of the numerals indicate the amino acid residues at the respective positions in the amino acid sequence of the wild-type GSHA shown as SEQ ID NO: 2 (namely, the amino acid residues before being mutated, indicated with one-letter code). For example, "L135" indicates the Leu residue at position 135 in the amino acid sequence of the wild-type GSHA shown as SEQ ID NO: 2.

As for the aforementioned mutation, the amino acid residues after substitution may be any amino acid residues other than the original amino acid residues, so long as the mutant GSHA has the γ-glutamylvaline synthetase activity. Specific examples of the amino acid residue after the substitution include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), which should be other than the original amino acid residues.

Specific examples of the "specific mutation" include a mutation corresponding to one or more mutations selected from the followings. That is, the "specific mutation" may include a mutation corresponding to one or more mutations selected from the followings. The "specific mutation" may be, for example, a mutation corresponding to any one of mutation selected from the followings, or may be a mutation corresponding to a combination of two or more mutations selected from the followings. The "specific mutation" may also be, for example, a mutation corresponding to a combination of one or more mutations selected from the followings, and a mutation other than the foregoing mutation at one or more amino acid residues selected from L135, Q144, Y241, N243, and Y300.
L135 (I, F, M, V, G, A, W, K, H, R, C, N, S, T),
Q144 (F, A, N, S, D, T, R, H, G, K, Y, W, C, M, P, V, L, I),
Y241 (A),
N243 (I, W, K, R, H),
Y300 (A, H, R, K).

In the aforementioned descriptions, the meanings of the numerals and the letters on the left side of the numerals are the same as those described above. The letters in the parentheses on the right side of the numerals indicate the amino acid residues (one-letter code) after being mutated. Namely, for example, "L135 (I, F, M, V, G, A, W, K, H, R, C, N, S, T)" means a mutation that the Leu residue at position 135 in the amino acid sequence of the wild-type GSHA shown as SEQ ID NO: 2 is replaced with any one of amino acid residues of Ile, Phe, Met, Val, Gly, Ala, Trp, Lys, His, Arg, Cys, Asn, Ser, and Thr. The amino acid residues after being mutated may also be mentioned without parenthesis. That is, for example, "L135I" means a mutation that the Leu residue at position 135 in the amino acid sequence of the wild-type GSHA shown as SEQ ID NO: 2 is replaced with an Ile residue.

Combination of the mutations is not particularly limited. Specific examples of combination of the mutations include the following combinations:

L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144R/N243F, Q144D/N243W, Q144D/N243F, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, L135T/Q144L.

In the aforementioned descriptions, the meanings of the numerals and the letters on the left and right sides of the numerals are the same as those described above. In the aforementioned descriptions, two ore more mutations separated with "/" indicate a double or more multiple mutation. That is, for example, "L135I/Q144R" indicates a double mutation of L135I and Q144R.

Also, examples of mutations with which a significant increase of the γ-glutamylvaline synthetase activity (specific activity) was observed in the Examples include the following mutations:

L135 (I, M, V, G, A, K, H, C, N, S, T),
Q144 (F, A, S, D, T, R, H, K, Y, W, C, M, P, V, L, I),
N243 (R, H),
Y300 (R, K),
L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144P, L135V/Q144W, L135V/Q144H, L135V/Q144E, L135V/Q144N, L135V/Q144S, L135D/Q144L, L135C/Q144L, L135N/Q144L, L135S/Q144L, L135T/Q144L.

A "mutation corresponding to a mutation of an amino acid residue at position n in the amino acid sequence shown as SEQ ID NO: 2" in the amino acid sequence of an arbitrary wild-type GSHA means a mutation at an amino acid residue corresponding to the amino acid residue at position n in the amino acid sequence shown as SEQ ID NO: 2. That is, for example, a "mutation corresponding to L135I" indicates a mutation that an amino acid residue corresponding to the Leu residue at position 135 (L135) in the amino acid sequence of wild-type GSHA shown as SEQ ID NO: 2 is replaced with an Ile residue. The "amino acid residue corresponding to L135" mentioned here may typically be a Leu residue, but may not be a Leu residue. Namely, for example, the "mutation corresponding to L135I" is not limited to a mutation that when the "amino acid residue corresponding to L135" is a Leu residue, the Leu residue is replaced with an Ile residue, but includes a mutation that when the "amino acid residue corresponding to L135" is Lys, Arg, His, Ala, Val, Gly, Ser, Thr, Pro, Phe, Trp, Tyr, Cys, Met, Asp, Glu, Asn, or Gln residue, this amino acid residue is replaced with an Ile residue. The same shall apply to the other mutations.

An "amino acid residue corresponding to the amino acid residue at position n in the amino acid sequence shown as SEQ ID NO: 2" in the amino acid sequence of an arbitrary wild-type GSHA means an amino acid residue corresponding to the amino acid residue at position n in the amino acid sequence shown as SEQ ID NO: 2 in an alignment of the target amino acid sequence of wild-type GSHA and the amino acid sequence of SEQ ID NO: 2. That is, as for the aforementioned mutation, the position of an amino acid residue does not necessarily indicate an absolute position in the amino acid sequence of a wild-type GSHA, but indicates a relative position based on the amino acid sequence shown as SEQ ID NO: 2. For example, when one amino acid residue is deleted at a position on the N-terminus side of position n in the wild-type GSHA consisting of the amino acid sequence shown as SEQ ID NO: 2, the amino acid residue originally at position n becomes an (n−1)th amino acid residue counted from the N-terminus, but it is regarded as the "amino acid residue corresponding to the amino acid residue at position n in the amino acid sequence shown as SEQ ID NO: 2". Similarly, for example, when an amino acid residue at position 100 in the amino acid sequence of a GSHA homologue of a certain microorganism corresponds to position 101 of the amino acid sequence shown as SEQ ID NO: 2, this amino acid residue is the "amino acid residue corresponding to the amino acid residue at position 101 in the amino acid sequence shown as SEQ ID NO: 2" in the GSHA homologue.

Such alignment can be performed by, for example, using known gene analysis software. Specific examples of such software include DNASIS produced by Hitachi Solutions, GENETYX produced by Genetyx, ClustalW opened to the public by DDBJ, and so forth (Elizabeth C. Tyler et al., Computers and Biomedical Research, 24(1), 72-96, 1991; Barton G. J. et al., Journal of Molecular Biology, 198 (2), 327-37, 1987; Thompson J D et al., Nucleic Acid Research, 22 (22), 4673-80, 1994).

<2> Production of Mutant Glutamate-cysteine Ligase (Mutant GSHA)

A mutant GSHA can be produced by making a host having a mutant gshA gene express the mutant gshA gene. The host having a mutant gshA gene can be obtained by introducing a mutant gshA gene into an appropriate host. "Introducing a mutant gshA gene into a host" also includes modifying the gshA gene on the chromosome of the host so as to have the "specific mutation". A host having a mutant gshA gene is also referred to as host having a mutant GSHA. A mutant GSHA can also be produced by expressing a mutant gshA gene in a cell-free protein synthesis system.

A mutant gshA gene can be obtained by, for example, modifying a wild-type gshA gene so that the encoded protein has the aforementioned "specific mutation". The original wild-type gshA gene to be modified can be obtained by, for example, cloning from an organism having a wild-type gshA gene, or chemical synthesis. A mutant gshA gene can also be obtained without using a wild-type gshA gene. For example, a mutant gshA gene may be directly obtained by chemical synthesis etc., or a mutant gshA gene may be further modified to obtain another mutant gshA gene.

Modification of a gene can be performed by a known method. For example, by the site-specific mutagenesis method, an objective mutation can be introduced into a target site of DNA. Examples of the site-specific mutagenesis method include a method using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987).

The host is not particularly limited so long as it can express a functional mutant GSHA. Examples of the host include, for example, bacteria, actinomycetes, yeast, fungi, plant cells, insect cells, and animal cells. Preferred examples of the host include microorganisms such as bacteria and yeast. More preferred examples of the host include bacteria. Examples of the bacteria include gram-negative bacteria and gram-positive bacteria. Examples of the gram-negative bacteria include, for example, bacteria belonging to the family Enterobacteriaceae, such as *Escherichia* bacteria, *Enterobacter* bacteria, and *Pantoea* bacteria. Examples of the gram-positive bacteria include *Bacillus* bacteria, and coryneform bacteria such as *Corynebacterium* bacteria. As the host, *Escherichia coli* can be especially preferably used.

The method for introducing a mutant gshA gene into a host is not particularly limited. In a host, a mutant gshA gene may be harbored in such a manner that it can be expressed under control of a promoter that functions in the host. In the host, the mutant gshA gene may exist on a vector autonomously replicable out of the chromosome such as plasmid, or may be introduced into the chromosome. The host may have only one copy of a mutant gshA gene, or may have two or more copies of a mutant gshA gene. The host may have only one kind of mutant gshA gene, or may have two or more kinds of mutant gshA genes.

The promoter for expressing a mutant gshA gene is not particularly limited so long as it is a promoter that functions in the host. The "promoter that functions in a host" refers to a promoter that shows a promoter activity in the host. The promoter may be a promoter derived from the host, or a heterologous promoter. The promoter may be the native promoter of the gshA gene, or may be a promoter of another gene. The promoter is preferably a promoter stronger than the native promoter of the gshA gene. Examples of strong promoters that function in Enterobacteriaceae bacteria, such as *Escherichia coli*, include, for example, T7 promoter, trp promoter, trc promoter, lac promoter, tac promoter, tet promoter, araBAD promoter, rpoH promoter, PR promoter, and PL promoter. Examples of strong promoters that function in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Further, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the mutant gshA gene. The terminator is not particularly limited so long as it functions in the bacterium of the present invention. The terminator may be a terminator derived from the host, or a heterogenous terminator. The terminator may be the native terminator of the gshA gene, or a terminator of another gene. Specific examples of the terminator include, for example, T7 terminator, T4 terminator, fd phage terminator, tet terminator, and trpA terminator.

A mutant gshA gene can be introduced into a host, for example, by using a vector containing the gene. A vector containing a mutant gshA gene is also referred to as expression vector or recombinant vector for a mutant gshA gene. The expression vector for a mutant gshA gene can be constructed by, for example, ligating a DNA fragment containing the mutant gshA gene with a vector that functions in the host. By transforming the host with the expression vector for a mutant gshA gene, a transformant into which the vector has been introduced is obtained, i.e. the gene can be introduced into the host. As the vector, a vector autonomously replicable in the cell of the host can be used. The vector is preferably a multi-copy vector. Further, the vector preferably has a marker such as an antibiotic resistance gene for selection of transformant. Further, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC, and the broad host spectrum vector RSF1010. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799. When the expression vector is constructed, for example, a mutant gshA gene having a native promoter region as it is may be incorporated into a vector, a coding region of a mutant GSHA ligated downstream from such a promoter as mentioned above may be incorporated into a vector, or a coding region of a mutant GSHA may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

A mutant gshA gene can also be introduced into, for example, a chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the production of an objective substance as a target. Further, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a mutant gshA gene having a native promoter region as it is may be incorporated into a chromosome, a coding region for a mutant GSHA ligated downstream from such a promoter as mentioned above may be incorporated into a chromosome, or a coding region for a mutant GSHA may be incorporated into a chromosome downstream from a promoter originally contained in the chromosome.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited, and conventionally known methods can be used. Examples of transformation method include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167), and so forth. Further, as the transformation method, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, as the transformation method, the electric pulse method reported for coryneform bacteria (Japanese Patent Laid-open (Kokai) No. 2-207791) can also be used.

The host for expressing a mutant gshA gene may or may not have a wild-type gshA gene. It is preferred that the host for expressing a mutant gshA gene does not have a wild-type gshA gene. A host not having a wild-type gshA gene can be obtained by disrupting the wild-type gshA gene on the chromosome. The method for disrupting a gene will be explained later. For example, a host not having a wild-type gshA gene but having a mutant gshA gene can be obtained by replacing the wild-type gshA gene on the chromosome with the mutant gshA gene. In order to replace the wild-type gshA gene with the mutant gshA gene, there can be used, for example, such methods as the method utilizing the method called "Red driven integration" (Datsenko, K. A, and Wanner, B. L., Proc. Natl. Acad. Sci. USA, 97:6640-6645 (2000)), and an excisive system derived from λ phage (Cho, E. H., Gumport, R. I., Gardner, J. F., J. Bacteriol., 184:5200-5203 (2002)) in combination, and the method for introducing a point mutation into a gene, which applies the foregoing method (Heermann, R et al., Microbial Cell Factories, 7:14 (2008)).

The host for expressing a mutant gshA gene may also have been modified so that the activity of a protein that participates in decomposition of a γ-glutamyl peptide is reduced. Examples of the protein that participates in decomposition of a γ-glutamyl peptide include γ-glutamyltransferase (GGT). By reducing the activity of GGT, decomposition of γ-Glu-Val and γ-Glu-Val-Gly can be suppressed. The activity of GGT can be reduced by such a means as disrupting the ggt gene encoding GGT. As an example, the nucleotide sequence of the ggt gene of Escherichia coli, and the amino acid sequence of the protein encoded by that gene are shown as SEQ ID NOS: 5 and 6, respectively.

Hereafter, the methods for reducing the activity of a protein will be explained.

The expression "the activity of a protein is reduced" means that the activity of the protein per cell is reduced as compared with that of a non-modified strain, such as a wild-type strain and parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0%, as compared with that of a non-modified strain.

The modification for reducing the activity of a protein is attained by, for example, reducing the expression of a gene encoding the protein. The expression "the expression of a gene is reduced" means that the expression of the gene per cell is reduced as compared with that of a non-modified strain such as a wild-type strain and parent strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0%, as compared with that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, preferably one or more nucleotides, more preferably two or more nucleotides, particularly preferably three or more nucleotides, of the expression control sequence are modified. Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Further, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Further, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient type gene modified so that a part of the gene is deleted and thereby the gene is unable to produce a protein that normally functions, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Further, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that of a non-modified strain.

Disruption of a gene can be confirmed by determining nucleotide sequence of a part or the whole of the gene, restriction enzyme map, full length, or the like of the gene depending on the means used for the disruption.

By culturing a host obtained as described above, into which a mutant gshA gene has been introduced, a mutant GSHA can be expressed. Conditions for culture of the host and induction of gene expression may be chosen as required depending on various conditions such as type of marker, type of promoter, and type of the host. The medium used for the culture is not be particularly limited, so long as the host can proliferate in the medium and express a mutant GSHA. As the medium, for example, a usual medium that contains a carbon source, nitrogen source, sulfur source, inorganic ions, and other organic components as required can be used.

Examples of the carbon source include saccharides such as glucose, fructose, sucrose, molasses, and starch hydrolysate, alcohols such as glycerol and ethanol, and organic acids such as fumaric acid, citric acid, and succinic acid.

Examples of the nitrogen source include inorganic ammonium salts such as ammonium sulfate, ammonium chloride, and ammonium phosphate, organic nitrogen such as soybean hydrolysate, ammonia gas, and aqueous ammonia.

Examples of the sulfur source include inorganic sulfur compounds, such as sulfates, sulfites, sulfides, hyposulfites, and thiosulfates.

Examples of the inorganic ions include calcium ion, magnesium ion, manganese ion, potassium ion, iron ion, and phosphoric acid ion.

Examples of the other organic components include organic trace amount nutrients. Examples of the organic trace amount nutrients include required substances such as vitamin $B_1$, yeast extract containing such substances, and so forth.

Culture temperature may be, for example, 20 to 45° C., preferably 24 to 45° C. The culture is preferably performed as aeration culture. In the aeration culture, oxygen concentration may be adjusted to 5 to 50%, preferably about 10%, with respect to the saturated concentration. pH during the culture is preferably 5 to 9. For adjusting pH, inorganic or organic acidic or alkaline substances, such as calcium carbonate, ammonia gas, and aqueous ammonia, can be used.

By performing the culture preferably for about 10 to 120 hours under such conditions as mentioned above, a culture broth containing a mutant GSHA is obtained. The mutant GSHA can be accumulated in, for example, microbial cells of the host. The term "microbial cell" may be appropriately read as "cell" depending on type of the host. Depending on the host to be used and design of the mutant gshA gene, it is also possible to accumulate the mutant GSHA in the periplasm, or to produce the mutant GSHA out of the cells by secretory production.

The mutant GSHA may be used in a state that it is contained in microbial cells or the like, or may be separated and purified from microbial cells or the like to be used as a crude enzyme fraction or a purified enzyme, as required.

That is, for example, when the mutant GSHA is accumulated in microbial cells of the host, by subjecting the cells to disruption, lysis, extraction, etc. as required, the mutant GSHA can be collected. The microbial cells can be collected from the culture broth by centrifugation or the like. Disruption, lysis, extraction, etc. of the cells can be performed by known methods. Examples of such methods include, for example, disruption by ultrasonication, disruption in Dyno-Mill, disruption in bead mill, disruption with French press, and lysozyme treatment. These methods may be independently used, or may be used in an appropriate combination. Also, for example, when the mutant GSHA is accumulated in the medium, a culture supernatant can be obtained by centrifugation or the like, and the mutant GSHA can be collected from the culture supernatant.

The mutant GSHA can be purified by known methods used for purification of enzymes. Examples of such methods include, for example, ammonium sulfate fractionation, ion exchange chromatography, hydrophobic chromatography, affinity chromatography, gel filtration chromatography, and isoelectric precipitation. These methods may be independently used, or may be used in an appropriate combination. The mutant GSHA may be purified to a desired extent. For example, when the mutant GSHA is contaminated with an ingredient that participates in decomposition of γ-glutamyl peptides, such as GGT, it is preferable to remove such an ingredient.

The purified mutant GSHA can be used as the "mutant GSHA" used in the methods of the present invention. The mutant GSHA may be used in a free form, or may be used as an immobilized enzyme immobilized on a solid phase of resin etc.

Not only the purified mutant GSHA, but also an arbitrary fraction containing a mutant GSHA may be used as the "mutant GSHA" in the methods of the present invention. Such a fraction containing a mutant GSHA is not particularly limited, so long as it contains a mutant GSHA so that the mutant GSHA can act on Glu and Val. Examples of such a fraction include, for example, a culture broth of a host having a mutant gshA gene (host having a mutant GSHA), microbial cells collected from such a culture broth (cultured microbial cells), processed products of such microbial cells such as disruption product of the cells, lysate of the cells, extract of the cells (cell-free extract), and immobilized cells obtained by immobilizing such cells as mentioned above on a carrier such as acrylamide and carrageenan, culture supernatant collected from such a culture broth, partially purified products of these (roughly purified products), and combinations of these. These fractions each may be used alone, or may be used together with a purified mutant GSHA.

<3> Glutathione Synthetase (GSHB) and Production Thereof

"Glutathione synthetase" is generally known as an enzyme having an activity for catalyzing the reaction of generating glutathione (γ-Glu-Cys-Gly), ADP, and phosphate by using γ-Glu-Cys, Gly, and ATP as the substrates (EC 6.3.2.3). In the present invention, this activity is also referred to as "glutathione synthetase activity". In the present invention, glutathione synthetase is also referred to as "GSHB".

In the present invention, an activity for catalyzing the reaction of generating γ-Glu-Val-Gly, ADP, and phosphate using γ-Glu-Val, Gly, and ATP as substrates is also referred to as "γ-glutamylvalylglycine synthetase activity" or "γ-Glu-Val-Gly generation activity".

In the present invention, as GSHB, one having the γ-glutamylvalylglycine synthetase activity is used. That is, in the present invention, the "glutathione synthetase (GSHB)" shall refer to a protein having the γ-glutamylvalylglycine synthetase activity.

In the present invention, so long as GSHB has the γ-glutamylvalylglycine synthetase activity, it may or may not have an activity for generating a γ-glutamyl tripeptide other than γ-glutamylvalylglycine. That is, in the present invention, for example, GSHB may or may not have the glutathione synthetase activity.

The γ-glutamylvalylglycine synthetase activity of GSHB can be measured by, for example, using an appropriate amount of GSHB with a reaction mixture composition of 12.5 mM γ-Glu-Val, 12.5 mM Gly, 12.5 mM ATP, 12.5 mM MgSO$_4$, 2 mM dithiothreitol, 100 mM Tris-HCl buffer (pH 8.0) at a reaction temperature of 37° C. for a reaction time of from 1 minute to 50 hours. The enzymatic activity for generating 1 µmol of γ-Glu-Val-Gly in 1 minute under the aforementioned conditions is defined as 1 U of the γ-glutamylvalylglycine synthetase activity.

Examples of GSHB include the GshB protein encoded by the gshB gene of *Escherichia coli* (GSHB of *Escherichia coli*), and the Gsh2 protein encoded by the GSH2 gene of *Saccharomyces cerevisiae* (GSHB of *Saccharomyces cerevisiae*). Examples of GSHB also include the mutant glutathione synthetase described in WO2013/054447. The nucleotide sequence of the gshB gene of the *Escherichia coli* K-12 MG1655 strain corresponds to the sequence of the positions 3,089,900 to 3,090,850 in the genome sequence registered at the NCBI database as GenBank accession NC_000913.3. The nucleotide sequence of the gshB gene of the *Escherichia coli* K-12 W3110 strain is identical to that of the MG1655 strain. The nucleotide sequence of the gshB gene of the MG1655 strain (gshB gene of the W3110 strain) is shown as SEQ ID NO: 3. The amino acid sequence of the protein encoded by this gene is shown as SEQ ID NO: 4. That is, GSHB may be, for example, a protein encoded by a gene having the nucleotide sequence shown as SEQ ID NO: 3. GSHB may also be, for example, a protein having the amino acid sequence shown as SEQ ID NO: 4. GSHB may also have a tag sequence, such as His tag. GSHB may also be a variant of the aforementioned GSHB, so long as it has the γ-glutamylvalylglycine synthetase activity. To such a variant, the aforementioned descriptions concerning variant of the wild-type GSHA can be applied mutatis mutandis.

GSHB can be produced by making a host having a gene encoding GSHB (also referred to as "gshB gene", but also includes those having a gene name different from gshB, such as GSH2 gene) express the gshB gene. Such a host having the gshB gene may be one obtained by introducing the gshB gene into an appropriate host, or may be one inherently having the gshB gene. The host having the gshB gene is also referred to as host having GSHB. Examples of such a host inherently having the gshB gene include such microorganisms as the *Escherichia coli* having the gshB gene, and *Saccharomyces cerevisiae* having the GSH2 gene mentioned above. A host inherently having the gshB gene may have been modified so that the expression of the gshB gene is increased. Examples of the means for increasing the expression of the gshB gene include increasing the copy number of the gshB gene, and improving the transcription efficiency of the gshB gene. The copy number of the gshB gene can be increased by introducing the gshB gene into a host. To the introduction of the gshB gene, the aforementioned descriptions concerning introduction of the mutant gshA gene can be applied mutatis mutandis. The gshB gene to be introduced may be a gene derived from the host, or heterogenous gene. The transcription efficiency of the gshB gene can be improved by replacing the promoter of the gshB gene with a stronger promoter. As such stronger promoter, the strong promoters mentioned above can be used. The host for expressing the gshB gene may have been modified so that the activity of a protein that participates in decomposition of γ-glutamyl peptides, such as γ-glutamyltransferase (GGT), is reduced. GSHB can also be produced by expressing the gshB gene in a cell-free protein synthesis system.

To the production of GSHB using a host having the gshB gene, the aforementioned descriptions concerning production of the mutant GSHA using a host into which a mutant gshA gene has been introduced can be applied mutatis mutandis. The produced GSHB (such as a purified GSHB and a fraction containing GSHB) can be used as "GSHB" in the methods of the present invention. GSHB may be independently produced, or may be produced together with a mutant GSHA. For example, GSHB and a mutant GSHA can be produced together by making a host having both a gshB gene and a mutant gshA gene express these genes.

<4> Method for Producing γ-glutamylvalylglycine (γ-Glu-Val-Gly)

The present invention provides a method for producing γ-Glu-Val using a mutant GSHA, and a method for producing γ-Glu-Val-Gly using a mutant GSHA. These methods are also collectively referred to as the "methods of the present invention".

<4-1> Enzymatic Method

The present invention provides a method for enzymatically producing γ-Glu-Val-Gly by using a mutant GSHA. This method is also referred to as the "method for producing γ-Glu-Val-Gly of the present invention (enzymatic method)".

In the present invention, Glu and Val can be reacted to generate γ-Glu-Val by using a mutant GSHA. That is, the present invention provides a method for producing γ-Glu-Val, which comprises (A) a step of allowing a mutant GSHA to act on Glu and Val to generate γ-Glu-Val. This method is also referred to as the "method for producing γ-Glu-Val of the present invention (enzymatic method)". The generated γ-Glu-Val can be collected from the reaction mixture, as required.

Further, by using the generated γ-Glu-Val as a raw material, γ-Glu-Val-Gly can be produced. As a method for producing γ-Glu-Val-Gly by using γ-Glu-Val as a raw material, the method of using glutathione synthetase (GSHB) is known (Japanese Patent Laid-open (Kokai) No. 2012-85637). Specifically, γ-Glu-Val and Gly can be reacted to generate γ-Glu-Val-Gly by using GSHB. That is, an embodiment of the method for producing γ-Glu-Val-Gly of the present invention (enzymatic method) (also referred to as the "first embodiment") is a method for producing γ-Glu-Val-Gly, which comprises (A) a step of allowing a mutant GSHA to act on Glu and Val to generate γ-Glu-Val, and (B) a step of allowing GSHB to act on γ-Glu-Val generated in the step (A) and Gly to generate γ-Glu-Val-Gly.

In the first embodiment, the step (A) and the step (B) may be carried out separately, or may be carried out simultaneously during a partial period or the whole period of the steps. That is, for example, the step (A) and the step (B) may be started simultaneously, or the step (B) may be started while the step (A) is in progress or after the step (A) is completed. The step (A) and the step (B) can be simultaneously started by making a mutant GSHA, GSHB, Glu, Val, and Gly coexist in a reaction system at the time of the start of the reaction. Alternatively, the step (A) can be started under the conditions that GSHB and/or Gly does not coexist in the reaction system, and the step (B) can be started by making GSHB and/or Gly coexist in the reaction system while the step (A) is in progress or after the step (A) is completed. Further, γ-Glu-Val generated in the step (A) may be collected, and the step (B) may be carried out by using the collected γ-Glu-Val. γ-Glu-Val may be subjected to such a treatment as purification, dilution, concentration, drying, and dissolution, as required, and then used for the step (B).

The step (A) of the method for producing γ-Glu-Val of the present invention (enzymatic method) can be carried out, for example, in the same manner as that for carrying out the step (A) of the first embodiment alone.

Also, in the present invention, Glu, Val, and Gly can be reacted to generate γ-Glu-Val-Gly by using a mutant GSHA and GSHB. That is, another embodiment of the method for producing γ-Glu-Val-Gly of the present invention (enzymatic method) (it is also referred to as the "second embodiment") is a method for producing γ-Glu-Val-Gly, which comprises (C) a step of allowing a mutant GSHA and GSHB to act on Glu, Val, and Gly to generate γ-Glu-Val-Gly. In the second embodiment, by making a mutant GSHA, GSHB, Glu, Val, and Gly coexist in a reaction system, the mutant GSHA and GSHB can be made to act on all of Glu, Val, and Gly to produce γ-Glu-Val-Gly.

In the methods of the present invention, the mutant GSHA and GSHB are also collectively referred to as "enzymes". Glu, Val, and Gly are also collectively referred to as "amino acids". γ-Glu-Val and γ-Glu-Val-Gly are also collectively referred to as "peptides". Glu, Val, Gly, and γ-Glu-Val are also collectively referred to as "substrates". The "substrates" may further include ATP, unless otherwise stated. A reaction of an enzyme and a substrate corresponding to the enzyme is also referred to as "enzymatic reaction".

The mode of the enzymes used for the methods of the present invention is as described above. That is, as each enzyme, for example, a purified enzyme, an arbitrary fraction containing the enzyme, or a combination of these can be used. As each enzyme, one kind of enzyme may be used, or two or more kinds of enzymes may be used in combination.

As each of the amino acids, a commercial product may be used, or one appropriately prepared and obtained may be used. The methods for producing an amino acid are not particularly limited, and, for example, known methods can be used. An amino acid can be produced by, for example, chemical synthesis, enzymatic reaction, or a combination of them. An amino acid can be produced by, for example, culturing a microorganism having an ability to produce the amino acid, and collecting the amino acid from culture. As a microorganism having an ability to produce an amino acid, for example, such amino acid-producing bacteria as described later can be used. An amino acid can also be produced by, for example, collecting the amino acid from agricultural, aquatic, and livestock products containing the amino acid. As each of the amino acids, a purified product purified to a desired extent may be used, or a material containing the amino acid may be used. Such a material containing an amino acid is not particularly limited so long as it contains an amino acid in such a manner that an enzyme can act on the amino acid. Specific examples of the material containing an amino acid include, for example, a culture broth obtained by culturing a microorganism having an ability to produce the amino acid, culture supernatant separated from the culture broth, cells separated from the culture broth, and processed products thereof such as concentrates (concentrated liquids) thereof and concentrated and dried products thereof.

In the methods of the present invention, the amino acids and peptides each may be a free compound, salt thereof, or mixture of them, unless otherwise stated. That is, the term "amino acid" may mean amino acid in the form of free compound, salt thereof, or mixture of them, unless otherwise stated. The term "peptide" may mean peptide in the form of free compound, salt thereof, or mixture of them, unless otherwise stated. The salt is not particularly limited so long as it is a chemically acceptable salt. When the produced γ-Glu-Val-Gly is used for oral use (for example, use as an additive for foods and drinks), the salt of γ-Glu-Val-Gly is not particularly limited so long as it is a chemically acceptable edible salt. Specific examples of the "chemically acceptable edible salt" include, for acidic groups such as carboxyl group, for example, ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Specific examples of the "chemically acceptable edible salt" include, for basic groups, for example, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. As the salt, one kind of salt may be used, or two or more kinds of salts may be used in combination.

The enzymatic reaction may be performed by the batch method or the column method. When the batch method is used, the enzymatic reaction can be performed by mixing the enzyme and the substrates in a reaction mixture contained in a reaction vessel. The enzymatic reaction may be performed in a stationary state, or with stirring. When the column method is used, the enzymatic reaction can be performed by passing a reaction mixture containing the substrates thorough a column filled with immobilized cells or immobilized enzyme. As the reaction mixture, water, buffer, or the like containing required ingredients can be used. The reaction mixture may contain, for example, the enzyme(s), substrates, ATP, and divalent metal ions. Combination of the ingredients used for the enzymatic reaction can be appropriately chosen according to type and implementation scheme of the step to be performed, such as whether two or more of steps are simultaneously carried out or not.

Both the mutant GSHA and GSHB use ATP for the enzymatic reaction. Therefore, ATP is supplied to the reaction system as required. That is, the reaction system (reaction mixture) may contain ATP. All of the aforementioned steps (A) to (C) can be carried out in the presence of ATP. The method for supplying ATP is not particularly limited so long as ATP can be used for the enzymatic reaction. ATP can be added to the reaction mixture in an arbitrary form, for example, in the form of powder or aqueous solution. ATP may also be supplied to the reaction system by, for example, a method for generating or regenerating ATP. As the method for generating or regenerating ATP, there are known the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-790 (1988)), the method of regenerating ATP by using polyphosphoric acid and polyphosphate kinase (Murata, K. et al., Agric. Biol. Chem., 52(6):1471-1477 (1988)), and so forth.

Also, for example, the mutant GSHA typically requires a divalent metal ion for the enzymatic reaction. Therefore, the reaction system (reaction mixture) may contain a divalent metal ion. All of the steps (A) to (C) can be carried out in the presence of a divalent metal ion. Preferred examples of the divalent metal ion include $Mg^{2+}$ and $Mn^{2+}$. The concentration of the divalent metal ion may be, for example, 1 to 200 mM.

Reaction conditions (pH of the reaction mixture, reaction temperature, reaction time, concentrations of various ingredients such as substrates and enzyme, etc.) are not particularly limited so long as γ-Glu-Val-Gly is generated.

pH of the reaction mixture may be, for example, usually 6.0 to 10.0, preferably 6.5 to 9.0.

The reaction temperature may be, for example, usually 15 to 50° C., preferably 15 to 45° C., more preferably 20 to 40° C.

The reaction time may be, for example, 5 minutes to 200 hours for each of the steps (A) and (B) of the first embodiment. The reaction time may be, for example, 5 minutes to 200 hours for the step (C) of the second embodiment. Flow rate of the reaction mixture may be, for example, such a rate that the reaction time should be within the range of the reaction time exemplified above.

The concentration of each of the substrates in the reaction mixture may be, for example, usually 0.1 to 2000 mM, preferably 1 to 2000 mM, more preferably 10 to 1000 mM.

Molar ratio of the substrates in the reaction mixture for the step (A) of the first embodiment may be set so that, for example, usually, Glu:Val:ATP is 1:1:1, and ratio of an arbitrary substrate may be changed within the range of 0.1 to 10. That is, for example, Glu:Val:ATP may be 0.1 to 10:0.1 to 10:0.1 to 10. As for the step (B) of the first embodiment, the molar ratio of the substrates in the reaction mixture may be set so that, for example, usually, γ-Glu-Val:Gly:ATP is 1:1:1, and ratio of an arbitrary substrate may be changed within the range of 0.1 to 10. That is, for example, γ-Glu-Val:Gly:ATP may be 0.1 to 10:0.1 to 10:0.1 to 10. Molar ratio of the substrates in the reaction mixture for the step (C) of the second embodiment may be set so that, for example, usually, Glu:Val:Gly:ATP is 1:1:1:2, ratio of an arbitrary substrate may be changed within the range of 0.1 to 10, and ratio of ATP may be changed within the range of 0.2 to 20. That is, for example, Glu:Val:Gly:ATP may be 0.1 to 10:0.1 to 10:0.1 to 10:0.2 to 20. When the step (A) and the step (B) are simultaneously carried out in the first embodiment, molar ratio of the substrates in the first embodiment may be determined with reference to the molar ratio of the substrates for the second embodiment, as required.

The amount of the enzyme to be used can be set on the basis of, for example, enzymatic activity. The amount of the mutant GSHA to be used may be, for example, usually 0.01 to 1000 U, preferably 0.1 to 500 U, more preferably 0.1 to 100 U, in terms of the γ-Glu-Val generation activity, with respect to 1 mmol of the total amount of Glu and Val. As for the step (B) of the first embodiment, the amount of GSHB to be used may be, for example, usually 0.01 to 1000 U, preferably 0.1 to 500 U, more preferably 0.1 to 100 U, in terms of the γ-Glu-Val-Gly generation activity, with respect to 1 mmol of the total amount of γ-Glu-Val and Gly. As for the step (C) of the second embodiment, the amount of GSHB to be used may be, for example, usually 0.01 to 1000 U, preferably 0.1 to 500 U, more preferably 0.1 to 100 U, in terms of the γ-Glu-Val-Gly generation activity, with respect to 1 mmol of the total amount of a half of the amount of Glu, a half of the amount of Val, and the whole amount of Gly. When the step (A) and the step (B) are simultaneously carried out in the first embodiment, the amount of GSHB to be used in the first embodiment may be determined with reference to the amount of GSHB to be used in the second embodiment, as required.

In any of the embodiments, in the course of the enzymatic reaction, the substrates, enzymes, and/or other ingredients may be additionally added to the reaction system independently or in an arbitrary combination. These ingredients may be added at one time, or two or more times, or they may be continuously added. The reaction conditions may be constant from the start to the end of the enzymatic reaction, or may change in the course of the enzymatic reaction. The expression "the reaction conditions change in the course of the enzymatic reaction" is not limited to cases where the reaction conditions temporally change, but also includes cases where the reaction conditions spatially change. The expression that "the reaction conditions spatially change" means that, for example, when the enzymatic reaction is performed by the column method, the reaction conditions such as reaction temperature and enzyme concentration are different depending on the position on the flowing pathway.

By carrying out the enzymatic reaction as described above, a reaction mixture containing γ-Glu-Val-Gly can be obtained. Generation of γ-Glu-Val-Gly can be confirmed by a known technique used for detection or identification of a compound. Examples of such a technique include, for example, HPLC, LC/MS, GC/MS, and NMR. These techniques may be independently used, or may be used in an appropriate combination. γ-Glu-Val-Gly can be collected from the reaction mixture as required. γ-Glu-Val-Gly can be collected by a known technique used for separation and purification of a compound. Examples of such a technique include, for example, various chromatography techniques such as ion exchange chromatography, reverse phase high performance liquid chromatography, and affinity chromatography, as well as crystallization and recrystallization from a solution. These techniques may be independently used, or may be used in an appropriate combination. The collected γ-Glu-Val-Gly may contain ingredients other than γ-Glu-Val-Gly, such as ingredients used for the production of γ-Glu-Val-Gly and moisture. γ-Glu-Val-Gly may be purified to a desired extent. γ-Glu-Val-Gly may be purified to a purity of, for example, 30% (w/w) or higher, 50% (w/w) or higher, 70% (w/w) or higher, 80% (w/w) or higher, 90% (w/w) or higher, or 95% (w/w) or higher. γ-Glu-Val can be collected in a manner similar to that for the collection of γ-Glu-Val-Gly.

<4-2> Fermentative Method

The present invention provides a method for producing γ-Glu-Val-Gly by fermentation using a mutant GSHA. This method is also referred to as the "method for producing γ-Glu-Val-Gly of the present invention (fermentative method)".

In the present invention, γ-Glu-Val can be produced from Glu and Val by fermentation by using a microorganism having a mutant GSHA. That is, the present invention provides a method for producing γ-Glu-Val, which comprises (A) a step of generating γ-Glu-Val from Glu and Val by culturing a microorganism having a mutant GSHA in a medium. This method is also referred to as the "method for producing γ-Glu-Val of the present invention (fermentative method)". The generated γ-Glu-Val can be collected from the culture as required.

Further, γ-Glu-Val-Gly can be produced by fermentation from γ-Glu-Val and Gly by using a microorganism having GSHB. That is, an embodiment of the method for producing γ-Glu-Val-Gly of the present invention (fermentative method) (also referred to as "third embodiment") is a method for producing γ-Glu-Val-Gly, which comprises (A) a step of generating γ-Glu-Val from Glu and Val by culturing a microorganism having a mutant GSHA in a medium, and (B) a step of generating γ-Glu-Val-Gly from γ-Glu-Val generated in the step (A) and Gly by culturing a microorganism having GSHB in a medium.

In the third embodiment, the step (A) and the step (B) may be carried out separately, or may be carried simultaneously during a partial period or the whole period of the steps. That is, for example, the step (A) and the step (B) may be started simultaneously, or the step (B) may be started while the step (A) is in progress or after the step (A) is completed. In the third embodiment, the step (A) and the step (B) may be carried out by using a microorganism having a mutant GSHA and another microorganism having GSHB, or may be carried out by using a single kind of microorganism having both a mutant GSHA and GSHB. For example, if a microorganism having both a mutant GSHA and GSHB is used, and it is cultured in a state that Glu, Val, and Gly are available, the step (A) and the step (B) can be simultaneously carried out. Further, γ-Glu-Val generated in the step (A) may be collected, and added to a medium to carry out the step (B). γ-Glu-Val may be subjected to such a treatment as purification, dilution, concentration, drying, and dissolution, as required, and then used for the step (B).

The step (A) of the method for producing γ-Glu-Val of the present invention (fermentative method) can be carried out, for example, in the same manner as that for carrying out the step (A) of the third embodiment alone.

Also, in the present invention, γ-Glu-Val-Gly can be produced by fermentation from Glu, Val, and Gly by using a microorganism having both a mutant GSHA and GSHB. That is, another embodiment of the method for producing γ-Glu-Val-Gly of the present invention (fermentative method) (also referred to as "fourth embodiment") is a method for producing γ-Glu-Val-Gly, which comprises (C) a step of generating γ-Glu-Val-Gly from Glu, Val, and Gly by culturing a microorganism having a mutant GSHA and GSHB in a medium.

In the fermentative method, such terms as enzymes, amino acids, peptides, substrates, and enzymatic reaction are used in the same meanings as those used for the enzymatic method. A microorganism having a mutant GSHA, microorganism having GSHB, and microorganism having a mutant GSHA and GSHB are also generically referred to as "microorganisms".

The method for supplying amino acids used as the substrates is not particularly limited so long as the amino acids can be used for the enzymatic reaction. For example, the amino acids each may be biosynthesized by a microorganism used in the corresponding step, may be added to the medium, or may be supplied by a combination of the foregoing means. That is, for example, all of Glu, Val, and Gly may be biosynthesized by a microorganism, or all of Glu, Val, and Gly may be added to the medium. Alternatively, for example, one or two kinds of amino acids among Glu, Val, and Gly may be biosynthesized by a microorganism, and the other amino acid(s) may be added to the medium. All of Glu, Val, and Gly may also be biosynthesized by a microorganism, and added to the medium.

That is, an embodiment of the method for producing γ-Glu-Val of the present invention (fermentative method) may be, for example, a method for producing γ-Glu-Val, which comprises (A1) a step of generating γ-Glu-Val by culturing a microorganism having a mutant GSHA in a medium containing Glu and Val, or a method for producing γ-Glu-Val, which comprises (A2) a step of generating γ-Glu-Val by culturing a microorganism having a mutant GSHA and having an ability to produce Glu and Val in a medium.

Also, an embodiment of the third embodiment may be, for example, a method for producing γ-Glu-Val-Gly, which comprises the step of (A1) or (A2), and the step of (B1) or (B2):

(A1) a step of generating γ-Glu-Val by culturing a microorganism having a mutant GSHA in a medium containing Glu and Val;
(A2) a step of generating γ-Glu-Val by culturing a microorganism having a mutant GSHA and having an ability to produce Glu and Val in a medium;
(B1) a step of generating γ-Glu-Val-Gly by culturing a microorganism having GSHB in a medium containing γ-Glu-Val generated in the step (A1) or (A2), and Gly;
(B2) a step of generating γ-Glu-Val-Gly by culturing a microorganism having GSHB and having an ability to produce Gly in a medium containing γ-Glu-Val generated in the step (A1) or (A2).

Further, an embodiment of the fourth embodiment may be, for example, a method for producing γ-Glu-Val-Gly, which comprises (C1) a step of generating γ-Glu-Val-Gly by culturing a microorganism having a mutant GSHA and GSHB in a medium containing Glu, Val, and Gly, or a method for producing γ-Glu-Val-Gly, which comprises (C2) a step of generating γ-Glu-Val-Gly by culturing a microorganism having a mutant GSHA and GSHB and having an ability to produce Glu, Val, and Gly in a medium.

As the microorganism having a mutant GSHA, such a microorganism having a mutant gshA gene as mentioned above can be used as it is, or after modification as required. As the microorganism having GSHB, such a microorganism having the gshB gene as mentioned above can be used as it is, or after modification as required. As the microorganism having a mutant GSHA and GSHB, such a microorganism having a mutant gshA gene and the gshB gene as mentioned above can be used as it is, or after modification as required.

The microorganism having an ability to produce an amino acid may be one inherently having the ability to produce an amino acid, or may be one modified to have the ability to produce an amino acid. A microorganism having an ability to produce an amino acid can be obtained by imparting an amino acid-producing ability to a microorganism, or by enhancing an amino acid-producing ability of a microorganism. Either the impartation or enhancement of an enzyme-producing ability, such as introduction of a mutant gshA gene and/or a gshB gene, or impartation or enhancement of an amino acid-producing ability may be carried out first. That is, a microorganism having a mutant GSHA and/or GSHB and having an ability to produce an amino acid may be obtained by modifying a microorganism having a mutant GSHA and/or GSHB to have an amino acid-producing ability, or may be obtained by modifying a microorganism having an amino acid-producing ability to have a mutant GSHA and/or GSHB. An L-amino acid-producing ability can be imparted or enhanced by methods conventionally employed in the breeding of amino acid-producing strains of coryneform bacteria, Escherichia bacteria, and so forth (see "Amino Acid Fermentation", Gakkai Shuppan Center Ltd., 1st Edition, published May 30, 1986, pp. 77-100). Such methods include, for example, acquiring an auxotrophic mutant strain, an L-amino acid analogue-resistant strain, or a metabolic regulation mutant strain, and constructing a recombinant strain in which the activity of an L-amino acid biosynthesis system enzyme is enhanced. An L-amino acid-producing ability can also be imparted or enhanced by reducing the activity of an enzyme that catalyzes a reaction branching away from biosynthetic pathway of a target L-amino acid to generate a compound other than the target L-amino acid.

Examples of L-glutamic acid-producing bacteria include a recombinant strain obtained by introducing the mviN gene having V197M mutation into an odhA-deficient strain obtained from the *Corynebacterium glutamicum* (*Brevibacterium lactofermentum*) ATCC 13869 strain (Japanese Patent Laid-open (Kokai) No. 2010-161970), the *Pantoea agglomerans* AJ13355 strain introduced with the gltA (citrate synthase) gene derived from *Brevibacterium lactofermentum* (Japanese Patent No. 4285582), an *Escherichia* bacterium having a mutant glutamine synthetase in which the tyrosine residue at position 397 is replaced with another amino acid residue (U.S. Patent Published Application No. 2003/0148474), and so forth. Examples of L-valine-producing bacteria include the *Escherichia coli* VL1970 strain (U.S. Pat. No. 5,658,766), an *Escherichia* bacterium having a mutation for requiring lipoic acid for growth thereof and/or a mutation for lacking H$^+$-ATPase, an *Escherichia* bacterium that is, in addition to these characteristics, intracellularly introduced with a DNA fragment containing the ilvGMEDA operon that expresses at least the ilvG, ilvM, ilvE, and ilvD genes, but does not express the threonine deaminase activity (WO96/06926), and so forth. That is, for example, by introducing any of these modifications into a microorganism, an amino acid-producing ability can be imparted or enhanced.

The microorganism may also have been modified so that the ability to uptake an amino acid added to the medium is improved. The microorganism may also have been modified so that the ability to excrete the generated γ-Glu-Val out of the cell is improved, or it may have been modified so that the ability to uptake γ-Glu-Val added to the medium is improved, depending on the scheme of use of the microorganism. The microorganism may also have been modified so that the ability to excrete the generated γ-Glu-Val-Gly out of the cell is improved.

Culture conditions are not particularly limited, so long as the microorganism can proliferate, and γ-Glu-Val-Gly is generated. For the culture conditions, the descriptions concerning the culture conditions for the method for producing a mutant GSHA mentioned above can be referred to.

Both the mutant GSHA and GSHB use ATP for the enzymatic reaction. Therefore, ATP is supplied to the reaction system as required. That is, the reaction system may contain ATP. All of the aforementioned steps (A) to (C) can be carried out in the presence of ATP. The method for supplying ATP is not particularly limited so long as ATP can be used for the enzymatic reaction. ATP may be, for example, generated by a microorganism used in each step, or supplied to the reaction system by such a method for generating or regenerating ATP as mentioned above. For supplying ATP, for example, there can be preferably used a co-culture system such as those realized by a method of making a microorganism of which ATP regenerating system based on the usual energy metabolism is enhanced, or a microorganism having an ability to regenerate ATP by the action of polyphosphate kinase coexist in the culture medium (Japanese Patent Publication (Kokoku) Nos. 7-16431 and 6-69386).

Also, for example, a mutant GSHA typically requires a divalent metal ion for the enzymatic reaction. Therefore, the reaction system may contain a divalent metal ion. All of the steps (A) to (C) mentioned above can be carried out in the presence of a divalent metal ion.

When a medium containing an amino acid is used, the amino acid may be contained in the medium from the start of the culture, or may be added to the medium at an arbitrary time during the culture. Although the time of the addition can be changed as required according to various conditions such as culture time, the amino acid may be added, for example, preferably 0 to 50 hours, more preferably 0.1 to 24 hours, particularly preferably 0.5 to 6 hours, before the end of the culture. The amino acid may be added at one time, or two or more times, or it may be continuously added. The concentration of each of the amino acids in the medium may be, for example, usually 0.1 to 2000 mM, preferably 1 to 2000 mM, more preferably 10 to 1000 mM. As for molar ratio of substrates in the medium, the descriptions concerning the molar ratio of substrates in the reaction mixture for the enzymatic method may be applied mutatis mutandis.

By performing culture as described above, a culture broth containing γ-Glu-Val-Gly can be obtained. Generation of γ-Glu-Val-Gly can be confirmed by a known technique used for detection or identification of a compound as described above. γ-Glu-Val-Gly can be collected from the culture broth as required. γ-Glu-Val-Gly can be collected by a known technique used for separation or purification of a compound as described above. When γ-Glu-Val-Gly is accumulated in the cells, for example, the cells can be disrupted by ultrasonication or the like, and γ-Glu-Val-Gly can be collected by the ion-exchange resin method or the like from supernatant obtained by removing the cells by centrifugation.

When the microorganism is yeast, and γ-Glu-Val-Gly is accumulated in the cells thereof, this yeast can be used for, for example, production of yeast extract containing γ-Glu-Val-Gly. That is, the present invention provides a method for producing yeast extract containing γ-Glu-Val-Gly, which comprises preparing yeast extract by using the yeast as a raw material. The yeast extract can be prepared from the yeast in the same manner as usual production of yeast extract. The yeast extract may be one obtained by hot water extraction of the yeast cells followed by treatment of the resulting extract, or one obtained by digestion of the yeast cells followed by treatment of the digested product. The obtained yeast extract may be concentrated, or may be dried to make it in the form of powder, as required.

EXAMPLES

Hereafter, the present invention will be more specifically explained with reference to examples.

Example 1

Construction of Expression Plasmid for Wild-type gshA Gene

In this example, by using the plasmid pSH1391 carrying the gshA gene of Escherichia coli and the gshB gene of Escherichia coli (Suzuki, H., et al., J. Bacteriol., 187:5861-5867 (2005)) as starting materials, an expression plasmid pTO1 for the wild-type gshA gene of Escherichia coli in which the start codon was replaced with ATG was constructed.

(1) Construction of pSH1391

The method for constructing the plasmid pSH1391 was as follows. For the purpose of obtaining the gshA gene of Escherichia coli, PCR was performed by using the genomic DNA of the Escherichia coli MG1655 strain (ATCC 47076) as the template, Pfu polymerase produced by Stratagene, and the primers of SEQ ID NOS: 7 and 8 (Table 1). A fragment of about 2.4 kb containing the gshA gene obtained by digesting the PCR product with PvuI/PstI, and a fragment of about 4.2 kb obtained by digesting pBR322 with PvuI/PstI were ligated. The Escherichia coli DH5α strain was transformed with the ligation reaction mixture, applied to the LB agar medium containing 20 μg/mL of tetracycline hydrochloride (Tc), and cultured at 37° C. for 18 hours. Plasmids were extracted from the colonies of the grown transformants by a known method, and a plasmid having the objective structure was named pFK68.

TABLE 1

| SEQ ID NO: | Sequence (5'→3') |
|---|---|
| 7 | GGGCGATCGCCATTGCGTAAAACATCGCGC |
| 8 | GGGAACTGCAGGCGCTTCCATC |

Similarly, for the purpose of obtaining the gshB gene of Escherichia coli, PCR was performed by using the genomic DNA of the Escherichia coli MG1655 strain (ATCC 47076) as the template, Pfu polymerase produced by Stratagene, and the primers of SEQ ID NOS: 9 and 10 (Table 2). A fragment of about 1.5 kb containing the gshB gene obtained by digesting the PCR product with HindIII/BamHI, and a fragment of about 2.7 kb obtained by digesting pUC18 with HindIII/BamHI were ligated. The Escherichia coli DH5α strain was transformed with the ligation reaction mixture, applied to the LB agar medium containing 100 μg/mL of ampicillin sodium salt (Amp), and cultured at 37° C. for 18 hours. Plasmids were extracted from the colonies of the grown transformants by a known method, and a plasmid having the objective structure was named pFK63.

TABLE 2

| SEQ ID NO: | Sequence (5'→3') |
|---|---|
| 9 | GGGAAGCTTCAGCAGTGGCAGAAG |
| 10 | GGGGGATCCTGGAGAGCAGGCATG |

Then, a fragment of about 5.9 kb containing the gshA gene obtained by digesting pFK68 with AatII/ScaI, and a fragment of about 1.9 kb containing the gshB gene obtained by digesting pFK63 with AatII/SmaI were ligated. The Escherichia coli DH5α strain was transformed with the ligation reaction mixture, applied to the LB agar medium containing 20 μg/mL of Tc, and cultured at 37° C. for 18 hours. Plasmids were extracted from the colonies of the grown transformants by a known method, and a plasmid having the objective structure was named pSH1388.

Then, a fragment of about 7.8 kb containing the gshA gene, the gshB gene, and the tetracycline resistance gene obtained by digesting pSH1388 with BanIII was dephosphorylated, and ligated with a fragment of 1.2 kb containing the kanamycin resistance gene obtained by treating pUC4K (Pharmacia) with AccI. The *Escherichia coli* DH5α strain was transformed with the ligation reaction mixture, applied to the LB agar medium containing 30 μg/mL of kanamycin sulfate (kan), and cultured at 37° C. for 18 hours. Plasmids were extracted from the colonies of the grown transformants by a known method, and a plasmid having a structure containing the kanamycin resistance gene and the tetracycline resistance gene in the same orientation was named pSH1391.

(2) Construction of pTO1 pET3-a (Novagen) was digested with SphI, blunt-ended, and digested with PvuII, and the obtained DNA fragment of about 3.1 kb was self-ligated to obtain a plasmid pSH1558. A fragment of about 2.4 kb containing the ampicillin resistance gene obtained by digesting pSH1558 with AatII/BglII, and a fragment of about 3.6 kb containing a partial fragment of the wild-type gshA gene of the *Escherichia coli* obtained by digesting pSH1391 with AatII/EglII were ligated. The *Escherichia coli* DH5α strain was transformed with the ligation reaction mixture, applied to the LB agar medium containing 100 μg/mL of Amp, and cultured at 37° C. for 18 hours. Plasmids were extracted from the colonies of the grown transformants by a known method, and a plasmid having the objective structure was named pSH1559.

Then, for the purpose of introducing a W100L mutation into the gshA gene, PCR was performed by using KOD-plus Polymerase of Toyobo, pSH1559 as the template, and the primers of SEQ ID NOS: 11 and 12 (Table 3) according to the protocol of the manufacturer. The obtained PCR product was digested with DpnI, and the *Escherichia coli* DH5α strain was transformed with the digestion reaction mixture, applied to the LB agar medium containing 100 μg/mL of Amp, and cultured at 37° C. for 18 hours. Plasmids were extracted from the colonies of the grown transformants by a known method, the nucleotide sequences thereof were confirmed by using ABI PRISM 310NT Genetic Analyzer (Applied-Biosystems), and a plasmid having the objective structure was named pSH1560.

TABLE 3

| SEQ ID NO: | Name of primer | Sequence (5'→3') |
|---|---|---|
| 11 | gshAW100Ls | GGCATACTTAACGGCAGCATCCGCT-CATCGCC |
| 12 | gshAW100Ln | GGCGATGAGCGGATGCTGCCGTTAAGTAT-GCC |

Then, for the purpose of replacing the start codon of the gshA gene with ATG (L1M mutation), PCR was performed by using KOD-plus Polymerase of Toyobo, pSH1560 as the template, and the primers of SEQ ID NOS: 13 and 14 (Table 4) according to the protocol of the manufacturer. The obtained PCR product was digested with DpnI, and the *Escherichia coli* DH5α strain was transformed with the digestion reaction mixture, applied to the LB agar medium containing 100 μg/mL of Amp, and cultured at 37° C. for 18 hours. Plasmids were extracted from the colonies of the grown transformants by a known method, the nucleotide sequences thereof were confirmed, and a plasmid having the objective structure was named pSH1561.

TABLE 4

| SEQ ID NO: | Name of primer | Sequence (5'→3') |
|---|---|---|
| 13 | gshAL1Ms | GATACGTCCGGGATCATATTGACCTCCCGCC |
| 14 | gshAL1Mn | GGCGGGAGGTCAATATGATCCCGGACGTATC |

For the purpose of obtaining a partial fragment of the gshA gene in which the start codon was replaced with ATG, but which did not have the W100L mutation, a fragment of about 4.9 kb containing the ampicillin resistance gene obtained by digesting pSH1561 with EcoRV/BglII, and a fragment of about 1.1 kb obtained by digesting pSH1559 with EcoRV/BglII were ligated. The *Escherichia coli* DH5α strain was transformed with the ligation reaction mixture, applied to the LB agar medium containing 100 μg/mL of Amp, and cultured at 37° C. for 18 hours. Plasmids were extracted from the colonies of the grown transformants by a known method, the nucleotide sequences thereof were confirmed, and a plasmid having the objective structure was named pSH1694.

For the purpose of obtaining the gshA gene of the full length in which the start codon was replaced with ATG, but which did not have the W100L mutation, a fragment of about 5.5 kb containing the kanamycin resistance gene obtained by digesting pSH1391 with AatII/BglII, and a fragment of about 3.6 kb obtained by digesting pSH1694 with AatII/BglII were ligated. The *Escherichia coli* DH5α strain was transformed with the ligation reaction mixture, applied to the LB agar medium containing 30 μg/mL of Kan, and cultured at 37° C. for 18 hours. Plasmids were extracted from the colonies of the grown transformants by a known method, the nucleotide sequences thereof were confirmed, and a plasmid having the objective structure was named pSH1695.

Then, for the purpose of eliminating the unnecessary gshB gene contained in pSH1695, pSH1695 was digested with AatII/KpnI, and a DNA containing the objective gshA gene was isolated by agarose gel electrophoresis, blunt-ended, and self-ligated. The *Escherichia coli* DH5α strain was transformed with the ligation reaction mixture, applied to the LB agar medium containing 30 μg/mL of Kan, and cultured at 37° C. for 18 hours. Plasmids were extracted from the colonies of the grown transformants by a known method, and a plasmid having the objective structure was named pTO1.

Example 2

Construction of Expression Plasmid for Mutant gshA Gene

In this example, expression plasmids for various mutant gshA genes were constructed from pTO1.

In order to construct mutant gshA genes, PCR was performed by using KOD-plus Polymerase of Toyobo, primers corresponding to various mutant gshA genes (SEQ ID NOS: 15 to 26), and pTO1 constructed in Example 1 as the template according to the protocol of the manufacturer. The relations between the mutations and the primers are shown in Table 5. In the table, the underlined parts correspond to the amino acid residues for which the mutation was introduced. Each of the obtained PCR products was digested with DpnI, and the *Escherichia coli* DH5α strain was transformed with the digestion reaction mixture, applied to the LB agar medium containing 30 μg/mL of Kan, and cultured at 37° C. for 18 hours. Plasmids were extracted from the colonies of the grown transformants by a known method, the nucleotide sequences thereof were confirmed, and a plasmid having the objective structure was obtained as an expression plasmid for the mutant gshA gene. The relations between the mutations and the plasmids are also shown in Table 5. The start codon of the gshA gene of *Escherichia coli* is originally TTG. However, since the start codon was replaced with ATG in pTO1, the start codon of the mutant gshA gene in each expression plasmid for mutant gshA gene is also ATG.

In order to evaluate the effect of the introduction of mutation by measuring the enzymatic activity using cell-free extract, the *Escherichia coli* SI97 strain was transformed with each expression plasmid for mutant gshA gene to obtain the strains shown in Table 5. Similarly, the *Escherichia coli* SI97 strain was transformed with the expression plasmid pTO1 for wild-type gshA gene to obtain TO22 strain. The *Escherichia coli* SI97 strain is a strain deficient in the ggt gene and the gshA gene of the *Escherichia coli* MG1655 strain (Suzuki, H., et al., J. Bacteriol., 187:5861-5867 (2005)). Use of the *Escherichia coli* SI97 strain as a host eliminates influence of the gene product of the gshA gene inherently possessed by *Escherichia coli* at the time of the measurement of the enzymatic activity. Use of the *Escherichia coli* SI97 strain as a host also eliminates influence of enzymatic decomposition of a peptide having γ-glutamyl bond as the enzymatic reaction product by the ggt gene product contained in the cell-free extract at the time of the measurement of the enzymatic activity.

were washed by suspending them in 5 mL of Tris-HCl buffer (pH 8.0), and collecting them again by centrifugation (4° C., 8,000 rpm, 5 minutes). The cells obtained as precipitates were suspended again in 3 mL of Tris-HCl buffer (pH 8.0), and disrupted by ultrasonication (190 W, 5 minutes) with cooling in ice water. The disrupted cell suspension was centrifuged (4° C., 8,000 rpm, 10 minutes), and the obtained supernatant was used as a cell-free extract.

The enzymatic activity was measured by using the cell-free extract. As the enzymatic activity, γ-Glu-Val generation activity and γ-Glu-Gly generation activity were measured.

The measurement conditions of the γ-Glu-Val generation activity were as follows. The composition of the reaction mixture consisted of 25 mM glutamic acid, 25 mM valine, 5 mM ATP, and 25 mM $MgSO_4$ in 20 mM Tris-HCl buffer (pH 8.0). The volume of the reaction mixture was 1 mL, and the enzymatic reaction was started by adding the cell-free extract. The reaction temperature was 37° C., and the reaction time was 0 to 120 minutes. For terminating the reaction, 100 w/v % trichloroacetic acid was added to the reaction mixture in a volume of 0.05 mL per 0.5 mL of the reaction mixture. After completion of the reaction, the generated γ-Glu-Val was quantified by HPLC.

When the γ-Glu-Gly generation activity was measured, valine in the aforementioned reaction mixture was replaced with glycine, and the generated γ-Glu-Gly was quantified.

The conditions of HPLC were as follows. As the column, Shim-pack Amino-Na produced by Shimadzu Corp. (particle size 5 microns, inner diameter 6 mm, length 100 mm)

TABLE 5

| SEQ ID NO: | Sequence (5'→3') | Mutation | Plasmid | Strain |
|---|---|---|---|---|
| 15 | GACGCTTTAAAACGCTGTAT<u>CTT</u>GAAGGGCTGAAAAATGC | R132L | pTO2 | TO3 |
| 16 | CGATTTTTCAGCCCTTC<u>AAG</u>ATACAGCGTTTTAAAGCGTC | | | |
| 17 | GACGCTTTAAAACGCTGTAT<u>GTT</u>GAAGGGCTGAAAAATGC | R132V | pTO4 | TO5 |
| 18 | CGATTTTTCAGCCCTTC<u>AAC</u>ATACAGCGTTTTAAAGCGTC | | | |
| 19 | GACGCTTTAAAACGCTGTAT<u>TTT</u>GAAGGGCTGAAAAATGC | R132F | pTO8 | TO9 |
| 20 | CGATTTTTCAGCCCTTC<u>AAA</u>ATACAGCGTTTTAAAGCGTC | | | |
| 21 | GACGCTTTAAAACGCTGTAT<u>GCT</u>GAAGGGCTGAAAAATGC | R132A | pTO10 | TO11 |
| 22 | CGATTTTTCAGCCCTTC<u>AGC</u>ATACAGCGTTTTAAAGCGTC | | | |
| 23 | CTACGGCGCGCTGATG<u>TTT</u>ACCATTTCCGGCGTGCACTAC | Q144F | pTO18 | TO19 |
| 24 | GTAGTGCACGCCGGAAATGGT<u>AAA</u>CATCAGCGCGCCGTAG | | | |
| 25 | CTACGGCGCGCTGATG<u>GCA</u>ACCATTTCCGGCGTGCACTAC | Q144A | pTO20 | TO21 |
| 26 | GTAGTGCACGCCGGAAATGGT<u>TGC</u>CATCAGCGCGCCGTAG | | | |

Example 3

Evaluation of γ-glutamyl Dipeptide Generation Activity of Mutant GSHA

Each of the strains obtained in Example 2 was inoculated into 10 mL of the LB medium containing 30 μg/mL of Kan, and cultured overnight at 37° C. with shaking by 120 times/minute of reciprocal movement to obtain a preculture broth. The turbidity (600 nm) of the obtained preculture broth was measured, and the preculture broth was inoculated into 100 mL of the LB medium containing 30 μg/mL of Kan contained in a 500 mL-volume conical flask at an initial turbidity of 0.1. Culture was performed overnight at 37° C. with shaking by 100 times/minute of reciprocal movement, and then the cells were collected by centrifugation (4° C., 8,000 rpm, 5 minutes). The cells obtained as precipitates was used. As the eluents, a buffer A (66.6 mM citric acid, 1% perchloric acid, 7% ethanol, pH 2.8) and a buffer B (200 mM citric acid, 200 mM boric acid, 0.12 N NaOH, pH 10) were used. The column temperature was 60° C., and the flow rate was 0.6 mL/minute. The gradient of the eluents was constituted with 0% of buffer B for the period of 0 to 9 minutes, 0 to 7% of buffer B for 9 to 13 minutes, 7 to 8% of buffer B for 13 to 17.2 minutes, 11% of buffer B for 17.2 to 20.8 minutes, 50 to 58% of buffer B for 20.8 to 22 minutes, and 100% of buffer B for 22 to 28.8 minutes. Detection was performed with fluorescence wavelength of 450 nm and excitation wavelength of 350 nm by using o-phthalaldehyde as a detection reagent.

By the methods described above, the amounts of the generated γ-Glu-Val and γ-Glu-Gly were quantified, and specific activities were calculated. The results are shown in Table 6. In the table, data in the columns of "Reaction (A)", "Reaction (B)", and "(B)/(A)" indicated the specific activities of the γ-Glu-Gly generation activity, specific activities of the γ-Glu-Val generation activity, and ratios of the specific activity of γ-Glu-Val generation activity to the specific activity of γ-Glu-Gly generation activity, respectively.

TABLE 6

| Strain | Mutation | Reaction (A) Glu + Gly + ATP (U/mg) | Reaction (B) Glu + Val + ATP (U/mg) | (B)/(A) |
|---|---|---|---|---|
| TO22 | None | 0.0103 | 0.0007 | 0.07 |
| TO3 | R132L | 0.0022 | 0.0017 | 0.77 |
| TO5 | R132V | 0.0036 | 0.001 | 0.28 |
| TO9 | R132F | ND | 0.0005 | — |
| TO11 | R132A | ND | 0.0012 | — |
| TO19 | Q144F | 0.0055 | 0.0009 | 0.16 |
| TO21 | Q144A | 0.0017 | 0.0022 | 1.29 |

ND, below detection limit
—, Not indicatable

Example 4

Construction of Expression Plasmid for Wild-type gshA Gene

An expression plasmid pSF12-EcGshA for the gshA gene encoding the glutamate-cysteine ligase of *Escherichia coli* MG1655 (ATCC 47076) was constructed by the following procedure. The nucleotide sequence of the gshA gene and the amino acid sequence of GSHA encoded by that gene are shown as SEQ ID NOS: 1 and 2, respectively. Since the start codon of this gene was TTG, the start codon was replaced with ATG at the time of constructing pSF12-EcGshA. With pSF12-EcGshA, GSHA is expressed with a His tag added to the C-terminus.

First, a pUC18-derived plasmid pSF12-ggt containing the ggt gene encoding γ-glutamyl transpeptidase derived from the *Escherichia coli* W3110 strain (ATCC 27325) and the rpoH promoter (WO2013/051685A1) was digested with NdeI/PstI, and purified with QIAquick Gel Extraction Kit (Qiagen) to obtain a fragment of about 3.1 kb.

Then, PCR was performed by using the genomic DNA of the *Escherichia coli* MG1655 strain as the template, and Phusion Polymerase (New England Biolabs) according to the protocol of the manufacturer for 30 cycles with the conditions of 98° C. for 10 seconds, 55° C. for 15 seconds, and 72° C. for 25 seconds to obtain a fragment of about 1.6 kb. As the primers, the combination of the primers of SEQ ID NOS: 27 and 28 (Table 7) was used.

Then, a fragment of about 3.0 kb obtained by digesting pSF12-ggt with NdeI/PstI and the fragment of about 1.6 kb obtained by PCR were fused by using In-Fusion HD Cloning Kit (Clontech) according to the protocol of the manufacturer. The *Escherichia coli* JM109 strain was transformed with the fusion reaction mixture, applied to the LB agar medium (1.0% (w/v) peptone, 0.5% (w/v) yeast extract, 1.0% (w/v) NaCl, and 1.5% (w/v) agar) containing 100 μg/mL of ampicillin sodium salt (Amp), and cultured at 30° C. for 20 hours. Plasmids were extracted from the colonies of the grown transformants by a known method, the nucleotide sequences thereof were confirmed by using 3130 Genetic Analyzer (Life Technologies), and a plasmid having the objective structure was designated as pSF12-EcGshA.

TABLE 7

| SEQ ID NO: | Sequence (5'→3') |
|---|---|
| 27 | AAGGAGGAATCCATAATGATCCCGGACGTATCAC |
| 28 | CCAAGCTTGCATGCCTCAATGATGATGATGATGATGGGCGTGTTT TTCCAGCCACACCGCAAACGGTTCGG |

Example 5

Construction of Expression Plasmid for Mutant gshA Gene

In order to construct mutant gshA genes, PCR was performed by using the primers corresponding to various mutant gshA genes (SEQ ID NOS: 29 to 76) and pSF12-EcGshA described in Example 4 as the template with Quik Change Site-Directed Mutagenesis Kit (Stratagene) according to the protocol of the manufacturer. The relations between the mutations and the primers are shown in Table 8. In the table, the sequences indicated with capital letters correspond to the amino acid residues for which a mutation was introduced.

Each of the obtained PCR products was digested with DpnI, and the *Escherichia coli* JM109 strain was transformed with the digestion reaction mixture, applied to the LB agar medium containing 100 μg/mL of ampicillin sodium salt (Amp), and cultured at 30° C. for 20 hours. Plasmids were extracted from the colonies of the grown transformants by a known method, the nucleotide sequences thereof were confirmed by using 3130 Genetic Analyzer (Life Technologies), and a plasmid having the objective structure was obtained as an expression plasmid for the mutant gshA gene. Each of the plasmids into which the corresponding mutation was introduced was designated as a name generated by adding indication of type of the mutation to pSF12-EcGshA. For example, the plasmid having the mutant gshA gene encoding a mutant GSHA having a Q144F mutation was designated as pSF12-EcGshA-Q144F. Then, by further introducing a mutation in the same manner by using the expression plasmid for the mutant gshA gene obtained as described above as the template, expression plasmids for the mutant gshA gene having a double mutation were obtained, and similarly designated. For example, by further introducing Q144R mutation into pSF12-EcGshA-L135M used as the template, a plasmid having a mutant gshA gene encoding a mutant GSHA having a double mutation of L135M and Q144R (L135M/Q144R) was obtained, and designated as pSF12-EcGshA-L135M/Q144R. The start codon of the gshA gene of *Escherichia coli* is originally TTG. However, since the start codon was replaced with ATG in pSF12-EcGshA, the start codon of the mutant gshA gene in each expression plasmid for the mutant gshA gene is also ATG. With pSF12-EcGshA, GSHA is expressed with a His tag added to the C-terminus, and therefore, with each expression plasmid for the mutant gshA gene, GSHA is also expressed with a His tag added to the C-terminus.

TABLE 8

| SEQ ID NO: | Sequence (5'→3') | Mutation |
|---|---|---|
| 29 | ctgtatcgtgaagggATTaaaaatcgctacggc | L135I |
| 30 | GccgtagcgattttttAATcccttcacgatacag | |
| 31 | ctgtatcgtgaagggTTTaaaaatcgctacggc | L135F |
| 32 | GccgtagcgattttttAAAcccttcacgatacag | |
| 33 | ctgtatcgtgaagggATGaaaaatcgctacggc | L135M |
| 34 | GccgtagcgattttttCATcccttcacgatacag | |
| 35 | ctgtatcgtgaagggGTGaaaaatcgctacggc | L135V |
| 36 | GccgtagcgattttttCACcccttcacgatacag | |
| 37 | ctgtatcgtgaagggGGCaaaaatcgctacggc | L135G |
| 38 | gccgtagcgattttttGCCcccttcacgatacag | |
| 39 | ctgtatcgtgaagggGCCaaaaatcgctacggc | L135A |
| 40 | gccgtagcgattttttCGCcccttcacgatacag | |
| 41 | ctgtatcgtgaagggTGGaaaaatcgctacggc | L135W |
| 42 | GccgtagcgattttttCCAcccttcacgatacag | |
| 43 | ctgtatcgtgaagggAAAaaaaatcgctacggc | L135K |
| 44 | GccgtagcgattttttTTTcccttcacgatacag | |
| 45 | ctgtatcgtgaagggCATaaaaatcgctacggc | L135H |
| 46 | GccgtagcgattttttATGcccttcacgatacag | |
| 47 | gctacggcgcgctgatgTTCaccatttccggcgtgQ144F | |
| 48 | cacgccggaaatggtGAAcatcagcgcgccgtagc | |
| 49 | ctacggcgcgctgatgGCGaccatttccggcgtg | Q144A |
| 50 | cacgccggaaatggtCGCcatcagcgcgccgtag | |
| 51 | gctacggcgcgctgatgAACaccatttccggcgtgQ144N | |
| 52 | cacgccggaaatggtGTTcatcagcgcgccgtagc | |
| 53 | gctacggcgcgctgatgTCGaccatttccggcgtgQ144S | |
| 54 | cacgccggaaatggtCGAcatcagcgcgccgtagc | |
| 55 | gctacggcgcgctgatgGATaccatttccggcgtgQ144D | |
| 56 | cacgccggaaatggtATCcatcagcgcgccgtagc | |
| 57 | gctacggcgcgctgatgACCaccatttccggcgtgQ144T | |
| 58 | cacgccggaaatggtGGTcatcagcgcgccgtagc | |
| 59 | gctacggcgcgctgatgCGCaccatttccggcgtgQ144R | |
| 60 | cacgccggaaatggtGCGcatcagcgcgccgtagc | |
| 61 | gctacggcgcgctgatgCATaccatttccggcgtgQ144H | |
| 62 | cacgccggaaatggtATGcatcagcgcgccgtagc | |
| 63 | gctacggcgcgctgatgGGCaccatttccggcgtgQ144G | |
| 64 | cacgccggaaatggtGCCcatcagcgcgccgtagc | |
| 65 | gctacggcgcgctgatgAAAaccatttccggcgtgQ144K | |
| 66 | cacgccggaaatggtTTTcatcagcgcgccgtagc | |
| 67 | gctacggcgcgctgatgTATaccatttccggcgtgQ144Y | |
| 68 | cacgccggaaatggtATAcatcagcgcgccgtagc | |
| 69 | gctacggcgcgctgatgTGGaccatttccggcgtgQ144W | |
| 70 | cacgccggaaatggtCCAcatcagcgcgccgtagc | |
| 71 | gctacggcgcgctgatgTGCaccatttccggcgtgQ144C | |
| 72 | cacgccggaaatggtGCAcatcagcgcgccgtagc | |
| 73 | gctacggcgcgctgatgATGaccatttccggcgtgQ144M | |
| 74 | cacgccggaaatggtCATcatcagcgcgccgtagc | |
| 75 | gctacggcgcgctgatgCCGaccatttccggcgtgQ144P | |
| 76 | cacgccggaaatggtCGGcatcagcgcgccgtagc | |
| 77 | gctacggcgcgctgatgGTGaccatttccggcgtgQ144V | |
| 78 | cacgccggaaatggtCACcatcagcgcgccgtagc | |

TABLE 8-continued

| SEQ ID NO: | Sequence (5'→3') | Mutation |
|---|---|---|
| 79 | gctacggcgcgctgatgCTGaccatttccggcgtgQ144L | |
| 80 | cacgccggaaatggtCAGcatcagcgcgccgtagc | |
| 81 | gctacggcgcgctgatgATTaccatttccggcgtgQ144I | |
| 82 | cacgccggaaatggtAATcatcagcgcgccgtagc | |
| 83 | ttgagcgatctcggcGCGaccaataaatcgcaa | Y241A |
| 84 | ttgcgatttattggtCGCgccgagatcgctcaa | |
| 85 | gatctcggctataccATTaaatcgcaaagcaatc | N243I |
| 86 | gattgctttgcgatttAATggtatagccgagatc | |
| 87 | gatctcggctataccTTTaaatcgcaaagcaatc | N243F |
| 88 | gattgctttgcgatttAAAggtatagccgagatc | |
| 89 | gatctcggctataccTGGaaatcgcaaagcaatc | N243W |
| 90 | gattgctttgcgatttCCAggtatagccgagatc | |
| 91 | gatctcggctataccCCGaaatcgcaaagcaat | N243P |
| 92 | attgctttgcgatttCGGggtatagccgagatc | |
| 93 | gatctcggctataccTATaaatcgcaaagcaat | N243Y |
| 94 | AttgctttgcgatttATAggtatagccgagatc | |
| 95 | gatctcggctataccCGCaaatcgcaaagcaat | N243R |
| 96 | attgctttgcgatttGCGggtatagccgagatc | |
| 97 | gatctcggctataccTGCaaatcgcaaagcaat | N243C |
| 98 | attgctttgcgatttGCAggtatagccgagatc | |
| 99 | attgaaaacgaactgGCGgcgccgattcgtcca | Y300A |
| 100 | tggacgaatcggcgcCGCcagttcgttttcaat | |
| 101 | attgaaaacgaactgCATgcgccgattcgtcca | Y300H |
| 102 | tggacgaatcggcgcATGcagttcgttttcaat | |
| 103 | attgaaaacgaactgCGCgcgccgattcgtcca | Y300R |
| 104 | tggacgaatcggcgcGCGcagttcgttttcaat | |
| 105 | attgaaaacgaactgAAAgcgccgattcgtcca | Y300K |
| 106 | TggacgaatcggcgcTTTcagttcgttttcaat | |

Example 6

Purification of Wild-type and Mutant GSHAs of *Escherichia coli* MG1655 Strain, Having His Tag Added to C-terminus Each of the strains obtained in Examples 4 and 5 (i.e. *Escherichia coli* JM109 strains harboring the respective gshA gene expression plasmids) was inoculated into 3 mL of the LB medium (1.0% (w/v) peptone, 0.5% (w/v) yeast extract, 1.0% (w/v) NaCl) containing 100 μg/mL of Amp, and cultured at 30° C. for 20 hours with shaking by 120 times/minute of reciprocal movement to obtain a preculture broth. The obtained preculture broth in a volume of 150 μl was inoculated into 15 mL of the TB medium (1.2% (w/v) tryptone, 2.4% (w/v) yeast extract, 0.4% (w/v) glycerol, 0.23% (w/v) $KH_2PO_4$, and 1.25% (w/v) $K_2HPO_4$) containing 100 μg/mL of Amp contained in a 70 mL-volume test tube (q) 25 mm). Culture was performed at 30° C. for 20 hours with shaking by 120 times/minute of reciprocal movement, and then the cells were collected by centrifugation (4° C., 12,000 rpm, 5 minutes). The cells obtained as precipitates were suspended in 0.2 mL of a buffer (20 mM Tris-HCl (pH 8.0), 300 mM NaCl, 10 mM imidazole, and 15% glycerol), and disrupted by ultrasonication with cooling. The obtained disrupted cell suspension was centrifuged (4° C., 29,100×g, 10 minutes), and the obtained supernatant was used as a cell-free extract.

The obtained cell-free extract was applied to Nickel Sepharose 6 Fast Flow Beads (GE Healthcare) equilibrated beforehand with a buffer (20 mM Tris-HCl (pH 8.0), 300 mM NaCl, 10 mM imidazole, and 15% glycerol), and the enzyme was eluted with an elution buffer (20 mM Tris-HCl (pH 8.0), 300 mM NaCl, 250 mM imidazole, and 15% glycerol) to obtain an active fraction. This active fraction was used as a purified GSHA for the following experiments.

Example 7

Purification of GSHB Derived from *Escherichia Coli* W3110 Strain, Having His Tag Added to C-terminus An expression plasmid pET-EcgshB for the gshB gene (SEQ ID NO: 3) encoding glutathione synthetase of the *Escherichia coli* W3110 strain (ATCC 27325) was constructed by the method described in Japanese Patent Laid-open (Kokai) No. 2012-85637. Then, the *Escherichia coli* BL21 (DE3) (Life Technologies) was transformed with pET-EcgshB to obtain *Escherichia coli* BL21 (DE3)/pET-EcgshB. The nucleotide sequence of the gshB gene and the amino acid sequence of GSHB encoded by that gene are shown as SEQ ID NOS: 3 and 4, respectively. With pET-EcgshB, GSHB is expressed with a His tag added to the C-terminus.

This strain was cultured by the same method as that used in Japanese Patent Laid-open (Kokai) No. 2012-85637. The cells were collected by centrifugation (12,000×g, 10 minutes), and washed with physiological saline (0.85% (w/v) NaCl), and then a cell suspension was prepared by using a buffer (20 mM Tris-HCl (pH 8.0), 300 mM NaCl, 10 mM imidazole, and 15% glycerol). The cell suspension was subjected to ultrasonication to disrupt the cells, and centrifuged (29,100×g, 15 minutes), and the obtained supernatant was used as a cell-free extract.

The obtained cell-free extract was applied to a HisTALON 5 mL column (Clontech) equilibrated beforehand with a buffer (20 mM Tris-HCl (pH 8.0), 300 mM NaCl, 10 mM imidazole, and 15% glycerol), and the enzyme was eluted with an elution buffer (20 mM Tris-HCl (pH 8.0), 300 mM NaCl, 200 mM imidazole, and 15% glycerol) to obtain an active fraction. Buffer change (20 mM Tris-HCl (pH 8.0), 300 mM NaCl, 15% glycerol) of the obtained active fraction was performed by using a PD-10 column (GE Healthcare) according to the instruction of the attached manual. The enzyme solution after the buffer change was used as a purified GSHB in the following experiments.

Example 8

Production of γ-glutamyl Dipeptide with Each Purified GSHA

The γ-Glu-Val synthesis activity and γ-Glu-Gly synthesis activity of each of the purified GSHAs obtained in Example 6 were measured.

The measurement conditions of the γ-Glu-Val generation activity were as follows. Composition of the reaction mixture consisted of 10 mM glutamic acid, 10 mM valine, 10 mM ATP, and 10 mM MgSO$_4$ in 100 mM Tris-HCl (pH 9.0). The volume of the reaction mixture was 0.2 mL, and the enzymatic reaction was started by adding the purified enzyme. At this time, the purified GSHA was added to the reaction mixture at a concentration of 0.1 g/L. The reaction temperature was 30° C., and the reaction time was 30 minutes. For terminating the reaction, 0.2 mL of 200 mM sulfuric acid was added per 0.2 mL of the reaction mixture. After completion of the reaction, the generated γ-Glu-Val was quantified by HPLC.

The quantification conditions for γ-Glu-Val were as follows. Synergi 4μ Hydro-RP 80A produced by Phenomenex (particle size 4 microns, inner diameter 4.6 mm, length 250 mm) was used as the column. As the eluent, a mixture consisting an eluent A (50 mM sodium dihydrogenphosphate (pH 2.5, adjusted with phosphoric acid)) and eluent B (1:1 (v/v) mixture of eluent A and acetonitrile) in a ratio of 93:7 (v/v) was used. The flow rate was 1.0 mL/minute, column temperature was 40° C., and UV detection wavelength was 210 nm.

When the γ-Glu-Gly generation activity was measured, valine in the aforementioned reaction mixture was replaced with glycine, and 0.025 g/L of the purified GSHA was added to the reaction mixture to perform the enzymatic reaction. The reaction was terminated in the same manner as described above, and then the generated γ-Glu-Gly was quantified.

The quantification conditions for γ-Glu-Gly were as follows. Inertsil ODS-3 produced by GL Science (particle size 5 microns, inner diameter 4.6 mm, length 250 mm) was used as the column. As the eluent, an eluent C (100 mM potassium dihydrogenphosphate, 5 mM sodium octanesulfonate (pH 2.2, adjusted with phosphoric acid)) was used. The flow rate was 1.5 mL/minute, column temperature was 40° C., and UV detection wavelength was 210 nm.

By the methods described above, the amounts of generated γ-Glu-Val and γ-Glu-Gly were quantified, and specific activities were calculated. The results are shown in Table 9. In the table, data in the columns of "Reaction (A)", "Reaction (B)", and "(B)/(A)" indicated the specific activities of the γ-Glu-Gly generation activity, specific activities of the γ-Glu-Val generation activity, and ratios of the specific activity of γ-Glu-Val generation activity to the specific activity of γ-Glu-Gly generation activity, respectively. The indication "GSHA-WT" mentioned in the table means wild-type GSHA.

TABLE 9

| Mutation | Reaction (A) Glu + Gly + ATP (U/mg) | Reaction (B) Glu + Val + ATP (U/mg) | (B)/(A) |
| --- | --- | --- | --- |
| GSHA-WT | 2.41 | 0.10 | 0.04 |
| L135I | 0.48 | 0.98 | 2.04 |
| L135F | ND | 0.14 | — |
| L135M | 0.03 | 0.78 | 26.00 |
| L135V | 1.60 | 2.60 | 1.63 |
| L135G | 1.07 | 1.62 | 1.51 |
| L135A | 1.28 | 2.29 | 1.79 |
| L135W | ND | 0.08 | — |
| L135K | 0.11 | 0.84 | 7.64 |
| L135H | 0.01 | 0.33 | 33.00 |
| Q144F | 2.00 | 0.98 | 0.49 |
| Q144A | 1.01 | 0.63 | 0.62 |
| Q144N | 0.24 | 0.18 | 0.75 |
| Q144S | 0.99 | 0.32 | 0.32 |
| Q144D | 0.01 | 0.22 | 22.00 |

TABLE 9-continued

| Mutation | Reaction (A) Glu + Gly + ATP (U/mg) | Reaction (B) Glu + Val + ATP (U/mg) | (B)/(A) |
|---|---|---|---|
| Q144T | 0.85 | 0.68 | 0.80 |
| Q144R | 0.06 | 0.42 | 7.00 |
| Q144H | 0.30 | 0.49 | 1.63 |
| Q144G | 0.11 | 0.10 | 0.91 |
| Q144K | 0.87 | 0.45 | 0.52 |
| Q144Y | 1.29 | 0.65 | 0.50 |
| Q144W | 0.10 | 0.25 | 2.50 |
| Q144C | 2.65 | 1.09 | 0.41 |
| Q144M | 5.11 | 0.75 | 0.15 |
| Q144P | 1.91 | 0.95 | 0.50 |
| Q144V | 1.67 | 0.81 | 0.49 |
| Q144L | 3.61 | 1.38 | 0.38 |
| Q144I | 0.18 | 0.30 | 1.67 |
| Y241A | 0.06 | 0.18 | 3.00 |
| N243I | 1.30 | 0.16 | 0.12 |
| N243W | 0.07 | 0.18 | 2.57 |
| Y300A | 0.01 | 0.14 | 14.00 |
| Y300H | 0.20 | 0.17 | 0.85 |
| Y300R | 0.40 | 0.46 | 1.15 |
| Y300K | 0.10 | 0.28 | 2.80 |
| L135I/Q144R | ND | 0.42 | — |
| L135I/Q144D | ND | 0.22 | — |
| L135I/Q144A | 1.42 | 1.92 | 1.35 |
| L135I/Q144L | 2.25 | 1.32 | 0.59 |
| L135I/N243W | 0.04 | 0.58 | 14.50 |
| L135I/N243F | 0.03 | 0.39 | 13.00 |
| L135F/Q144A | 0.02 | 1.43 | 71.50 |
| L135F/N243W | ND | 0.16 | — |
| L135M/Q144R | ND | 0.64 | — |
| L135M/Q144A | 0.28 | 0.44 | 1.57 |
| L135M/Q144L | 0.12 | 1.61 | 13.42 |
| L135M/N243W | 0.01 | 0.65 | 65.00 |
| L135M/N243F | ND | 0.13 | — |
| L135M/Q144H | ND | 1.23 | — |
| L135M/Q144N | ND | 0.67 | — |
| L135M/N243Y | ND | 0.19 | — |
| L135M/N243R | ND | 0.18 | — |
| L135M/N243C | 0.01 | 0.87 | 87.00 |
| L135V/Q144R | 0.10 | 1.27 | 12.70 |
| L135V/Q144D | ND | 0.22 | — |
| L135V/Q144A | 1.03 | 1.58 | 1.53 |
| L135V/Q144L | 0.64 | 2.13 | 3.33 |
| L135V/Q144V | 0.11 | 1.75 | 15.91 |
| L135V/Q144K | 0.31 | 1.80 | 5.81 |
| L135V/Q144C | 0.74 | 4.13 | 5.58 |
| L135V/Q144T | 0.04 | 1.44 | 36.00 |
| L135H/Q144R | ND | 1.24 | — |
| L135G/Q144L | 1.54 | 2.38 | 1.55 |
| L135A/Q144L | 1.08 | 2.33 | 2.16 |
| L135V/N243W | 0.05 | 0.72 | 14.40 |
| L135V/N243F | 0.03 | 0.40 | 13.33 |
| L135V/N243P | 0.19 | 1.09 | 5.74 |
| Q144R/N243W | ND | 0.28 | — |
| Q144R/N243F | 0.01 | 0.15 | 15.00 |
| Q144D/N243W | ND | 0.61 | — |
| Q144D/N243F | ND | 0.12 | — |
| Q144A/N243W | 0.22 | 0.65 | 2.95 |
| Q144A/N243F | 0.25 | 0.30 | 1.20 |
| Q144L/N243W | 1.02 | 1.26 | 1.24 |
| Q144L/N243F | 0.24 | 0.55 | 2.29 |

ND, below detection limit
—, Not indicatable

Example 9

Generation of γ-Glu-Val-Gly from Amino Acids Using Each Purified GSHA and Purified GSHB Generation of γ-Glu-Val-Gly (CAS 38837-70-6, also referred to as gluvalicine) from amino acids was examined by using each of the purified GSHAs obtained in Example 6 and the purified GSHB obtained in Example 7. The structural formula of γ-Glu-Val-Gly is shown below as the formula (I).

[Formula 1]

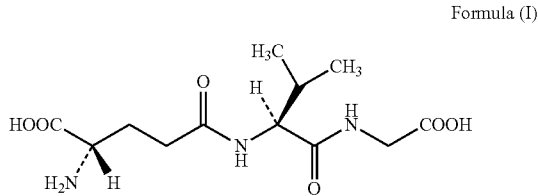

Formula (I)

The composition of the reaction mixture consisted of 10 mM glutamic acid, 10 mM valine, 10 mM glycine, 20 mM ATP, and 10 mM MgSO$_4$ in 100 mM Tris-HCl (pH 9.0). The volume of the reaction mixture was 0.2 mL, and the purified GSHA and purified GSHB were added to reaction mixture at 0.1 g/L and 0.05 g/L, respectively. The enzymatic reaction was started by adding the purified GSHA. The reaction temperature was 30° C., and the reaction time was 24 hours. For terminating the reaction, 0.2 mL of 200 mM sulfuric acid was added per 0.2 mL of the reaction mixture. After termination of the reaction, γ-Glu-Val-Gly was quantified in the same manner as the quantification of γ-Glu-Val performed in Example 8, and the generated amount thereof was calculated. The results and ratios (B)/(A) of the γ-Glu-Val synthesis activities to the γ-Glu-Gly synthesis activities shown in Example 8, Table 9 are shown in Table 10. The indication "GSHA-WT" mentioned in the table means wild-type GSHA.

TABLE 10

| Mutation | (B)/(A) | γ-Glu-Val-Gly (mM) |
|---|---|---|
| GSHA-WT | 0.04 | ND |
| L135F | — | 1.97 |
| L135M | 26.00 | 2.81 |
| Q144N | 0.75 | 0.30 |
| Q144D | 22.00 | 0.34 |
| Q144T | 0.80 | 0.23 |
| Q144R | 7.00 | 1.11 |
| Q144M | 0.15 | 0.02 |
| N243W | 2.57 | 0.70 |
| L135M/Q144R | — | 3.27 |
| Q144D/N243W | — | 2.99 |
| Q144A/N243F | 1.20 | 1.02 |
| Q144L/N243W | 1.24 | 0.79 |

ND, below detection limit
—, Not indicatable

Example 10

Acquisition of purified GSHA derived from Escherichia coli MG1655 strain having His tag added to C-terminus using cell-free protein synthesis system Purified enzymes of wild-type GSHA and mutant GSHAs derived from the Escherichia coli MG1655 (ATCC 47076) were obtained by entrusting the preparation thereof to the cell-free protein synthesis service of the independent administrative agency, Institute of Physical and Chemical Research (RIKEN) (http(colon)//www(dot)ynmr(dot)riken (dot)jp/fees/external_fee_2013(dot)html), and used in the following experiments. Eluted fractions obtained by affinity purification of the synthesized proteins using nickel were used as purified enzymes. For the elution, a buffer (50 mM sodium phosphate buffer (pH 8.0), 10% glycerol, 300 mM imidazole, 300 mM NaCl, 1 mM DTT) was used. Since the start codon of these genes was TTG, the start codon was replaced with ATG at the time of the synthesis of the proteins. The wild-type GSHA and mutant GSHAs were expressed 6 His residues added to the C-terminus. At the time of the protein synthesis, the expression amount improvement option of the cell-free protein synthesis service was used.

Example 11

Production of γ-glutamyl Dipeptide with Each Purified GSHA Synthesized in Cell-Free Protein Synthesis System The γ-Glu-Val synthesis activity and γ-Glu-Gly synthesis activity of each of the purified GSHAs obtained in Example 10 were measured.

The measurement conditions for the γ-Glu-Val generation activity were as follows. The composition of the reaction mixture consisted of 10 mM glutamic acid, 10 mM valine, 10 mM ATP, and 10 mM MgSO₄ in 100 mM Tris-HCl (pH 9.0). The volume of the reaction mixture was 0.2 mL, and the enzymatic reaction was started by adding the purified enzyme. The purified GSHA was added to the reaction mixture at 0.025 g/L. The reaction temperature was 30° C., and the reaction time was 60 minutes. For terminating the reaction, 0.2 mL of 200 mM sulfuric acid was added per 0.2 mL of the reaction mixture. After completion of the reaction, the generated γ-Glu-Val was quantified in the same manner as that described in Example 8.

When the γ-Glu-Gly generation activity was measured, valine in the aforementioned reaction mixture was replaced with glycine to perform the enzymatic reaction. The reaction was terminated in the same manner as that described above, and the generated γ-Glu-Gly was quantified by the method described in Example 8.

By the methods described above, the amounts of γ-Glu-Val and γ-Glu-Gly generated by the wild-type GSHA obtained in Example 10 were quantified, and specific activities were calculated. The results are shown in Table 11, row of "Wild-type GSHA (1)". Further, the results for the specific activities of the wild-type GSHA mentioned in Example 8, Table 9 are shown in Table 11, row of "Wild-type GSHA (2)". In the table, data in the columns of "Reaction (A)", "Reaction (B)", and "(B)/(A)" indicated the specific activities of the γ-Glu-Gly generation activity, specific activities of the γ-Glu-Val generation activity, and ratios of the specific activity of γ-Glu-Val generation activity to the specific activity of γ-Glu-Gly generation activity, respectively. As a result, it was observed that both wild-type GSHAs had comparable specific activities for the γ-Glu-Val generation activity and the γ-Glu-Gly generation activity.

TABLE 11

|  | Expression system | Reaction (A) Glu + Gly + ATP (U/mg) | Reaction (B) Glu + Val + ATP (U/mg) | (B)/(A) |
|---|---|---|---|---|
| Wild-type GSHA (1) | Cell-free synthesis system | 2.48 | 0.11 | 0.04 |
| Wild-type GSHA (2) | E. coli expression system | 2.41 | 0.10 | 0.04 |

Then, by the methods described above, the amounts of γ-Glu-Val and γ-Glu-Gly generated by the wild-type GSHA and mutant GSHAs obtained in Example 10 were quantified, and specific activities were calculated. The results are shown in Table 12. In the table, data in the columns of "Reaction (A)", "Reaction (B)", and "(B)/(A)" indicated the specific activities of the γ-Glu-Gly generation activity, specific activities of the γ-Glu-Val generation activity, and ratios of the specific activity of γ-Glu-Val generation activity to the specific activity of γ-Glu-Gly generation activity, respectively. The indication "GSHA-WT" mentioned in the table means wild-type GSHA.

TABLE 12

| Mutation | Reaction (A) Glu + Gly + ATP (U/mg) | Reaction (B) Glu + Val + ATP (U/mg) | (B)/(A) |
|---|---|---|---|
| GSHA-WT | 2.48 | 0.11 | 0.04 |
| L135R | 0.13 | 0.08 | 0.62 |
| L135C | 1.35 | 1.66 | 1.23 |
| L135N | 1.71 | 0.56 | 0.33 |
| L135S | 0.30 | 0.22 | 0.73 |
| L135T | 1.53 | 0.78 | 0.51 |
| N243K | 1.20 | 0.20 | 0.17 |
| N243R | 1.08 | 0.30 | 0.28 |
| N243H | 3.12 | 0.26 | 0.08 |
| L135M/Q144F | 0.17 | 1.44 | 8.47 |
| L135M/N243A | 0.28 | 1.00 | 3.57 |
| L135V/N243G | 0.71 | 1.92 | 2.70 |
| L135V/N243A | 3.07 | 3.68 | 1.20 |
| L135V/N243L | 0.88 | 1.60 | 1.82 |
| L135V/N243Y | 1.39 | 3.94 | 2.83 |
| L135V/N243K | 0.69 | 1.62 | 2.35 |
| L135V/N243R | 1.15 | 3.08 | 2.68 |
| L135V/N243H | 1.23 | 2.30 | 1.87 |
| L135V/N243D | 1.21 | 2.46 | 2.03 |
| L135V/N243E | 0.51 | 1.72 | 3.37 |
| L135V/N243C | 0.88 | 2.06 | 2.34 |
| L135V/N243Q | 0.70 | 1.98 | 2.83 |
| L135V/N243S | 1.55 | 2.58 | 1.66 |
| L135V/N243T | 1.38 | 2.62 | 1.90 |
| L135V/Q144I | 0.02 | 0.16 | 8.00 |
| L135V/Q144P | 0.93 | 2.52 | 2.71 |
| L135V/Q144W | 0.03 | 0.42 | 14.00 |
| L135V/Q144H | 0.22 | 1.88 | 8.55 |
| L135V/Q144E | 0.31 | 0.88 | 2.84 |
| L135V/Q144N | 0.10 | 1.18 | 11.80 |
| L135V/Q144S | 1.36 | 3.04 | 2.24 |
| L135K/Q144L | 0.08 | 0.16 | 2.00 |
| L135H/Q144L | 0.02 | 0.14 | 7.00 |
| L135D/Q144L | 0.06 | 0.26 | 4.33 |
| L135C/Q144L | 1.54 | 3.08 | 2.00 |
| L135Q/Q144L | 0.13 | 0.14 | 1.08 |
| L135N/Q144L | 1.00 | 2.44 | 2.44 |
| L135S/Q144L | 0.59 | 1.94 | 3.29 |
| L135T/Q144L | 3.59 | 3.22 | 0.90 |

INDUSTRIAL APPLICABILITY

The mutant GSHA of the present invention catalyzes the γ-Glu-Val generation reaction with selectively using Val as a substrate. Therefore, according to the present invention, γ-Glu-Val can be efficiently produced by using the mutant GSHA of the present invention with Glu and Val as raw materials, and γ-Glu-Val-Gly can further be produced by using γ-Glu-Val and Gly as raw materials. Also, according to the present invention, γ-Glu-Val-Gly can be efficiently produced by using the mutant GSHA of the present invention with Glu, Val, and Gly as raw materials.

EXPLANATION OF SEQUENCE LISTING

SEQ ID NO: 1, Nucleotide sequence of wild-type gshA gene of Escherichia coli MG1655 strain SEQ ID NO: 2, Amino acid sequence of wild-type GSHA protein of *Escherichia coli* MG1655 strain
SEQ ID NO: 3, Nucleotide sequence of gshB gene of *Escherichia coli* W3110 strain
SEQ ID NO: 4, Amino acid sequence of GSHB protein of *Escherichia coli* W3110 strain
SEQ ID NO: 5, Nucleotide sequence of ggt gene of *Escherichia coli* MG1655 strain
SEQ ID NO: 6, Amino acid sequence of GGT protein of *Escherichia coli* MG1655 strain
SEQ ID NOS: 7 to 106, Primers

The invention claimed is:

1. A method for producing γ-Glu-Val and/or a salt thereof, the method comprising:
   contacting a mutant glutamate-cysteine ligase with Glu and Val to produce γ-Glu-Val and/or a salt thereof,
   wherein the mutant glutamate-cysteine ligase comprises an amino acid sequence having at least 90% sequence identity to the amino acid sequence of SEQ ID NO: 2 wherein the amino acid residue corresponding to at least one residue selected from the group consisting of L135, Q144, Y241, N243, and Y300 of SEQ ID NO: 2 is mutated to a different amino acid in the mutant glutamate-cysteine ligase, and
   wherein the mutant has γ-glutamylvaline synthetase activity.

2. A method for producing γ-Glu-Val-Gly and/or a salt thereof, the method comprising:
   contacting a mutant glutamate-cysteine ligase with Glu and Val to produce γ-Glu-Val;
   contacting a glutathione synthetase with the produced γ-Glu-Val and Gly to produce γ-Glu-Val-Gly and/or a salt thereof,
   wherein the mutant glutamate-cysteine ligase comprises an amino acid sequence having at least 90% sequence identity to the amino acid sequence of SEQ ID NO: 2 wherein the amino acid residue corresponding to at least one residue selected from the group consisting of L135, Q144, Y241, N243, and Y300 of SEQ ID NO: 2 is mutated to a different amino acid in the mutant glutamate-cysteine ligase, and
   wherein the mutant has γ-glutamylvaline synthetase activity.

3. A method for producing γ-Glu-Val-Gly and/or a salt thereof, the method comprising:
   contacting a mutant glutamate-cysteine ligase and a glutathione synthetase with Glu, Val, and Gly to produce γ-Glu-Val-Gly and/or a salt thereof,
   wherein the mutant glutamate-cysteine ligase comprises an amino acid sequence having at least 90% sequence identity to the amino acid sequence of SEQ ID NO: 2 wherein the amino acid residue corresponding to at least one residue selected from the group consisting of L135, Q144, Y241, N243, and Y300 of SEQ ID NO: 2 is mutated to a different amino acid in the mutant glutamate-cysteine ligase, and
   wherein the mutant has γ-glutamylvaline synthetase activity.

4. The method according to claim 1, wherein the mutant glutamate-cysteine ligase is purified.

5. The method according to claim 1, wherein the mutant glutamate-cysteine ligase is immobilized.

6. The method according to claim 1, wherein the mutant glutamate-cysteine ligase is contained in:
   a culture broth of a microorganism producing the mutant glutamate-cysteine ligase,
   cultured cells of a microorganism producing the mutant glutamate-cysteine ligase, or
   a processed product of the cultured cells, wherein the processed product comprises the mutant glutamate-cysteine ligase.

7. The method according to claim 2, wherein the glutathione synthetase is contained in:
   a culture broth of a microorganism producing the glutathione synthetase,
   cultured cells of a microorganism producing the glutathione synthetase, or
   a processed product of the cultured cells, wherein the processed product comprises the glutathione synthetase.

8. The method according to claim 2, wherein the mutant glutamate-cysteine ligase and the glutathione synthetase are contained in:
   a culture broth of a microorganism producing the mutant glutamate-cysteine ligase and the glutathione synthetase,
   cultured cells of a microorganism producing the mutant glutamate-cysteine ligase and the glutathione synthetase, or
   a processed product of the cultured cells, wherein the processed product comprises the mutant glutamate-cysteine ligase and the glutathione synthetase.

9. The method according to claim 6, wherein a γ-glutamyltransferase gene is disrupted in the microorganism.

10. The method according to claim 6, wherein the microorganism is *Escherichia coli*.

11. The method according to claim 1, wherein the contacting of the mutant glutamate-cysteine ligase is carried out in the presence of ATP.

12. The method according to claim 1, wherein the amino acid residue is mutated in the mutant glutamate-cysteine ligase such that the mutation corresponds to at least one mutation in the amino acid sequence of SEQ ID NO: 2 selected from the group consisting of:
   L135I, L135F, L135M, L135V, L135G, L135A, L135W, L135K, L135H, L135R, L135C, L135N, L135S, L135T, Q144F, Q144A, Q144N, Q144S, Q144D, Q144T, Q144R, Q144H, Q144G, Q144K, Q144Y, Q144W, Q144C, Q144M, Q144P, Q144V, Q144L, Q144I, Y241A, N243I, N243W, N243K, N243R, N243H, Y300A, Y300H, Y300R, and Y300K.

13. The method according to claim 3, wherein the mutant glutamate-cysteine ligase is contained in:

a culture broth of a microorganism producing the mutant glutamate-cysteine ligase, cultured cells of a microorganism producing the mutant glutamate-cysteine ligase, or a processed product of the cultured cells, wherein the processed product comprises the mutant glutamate-cysteine ligase.

14. The method according to claim 3, wherein the mutant glutamate-cysteine ligase and the glutathione synthetase are contained in:

a culture broth of a microorganism producing the mutant glutamate-cysteine ligase and the glutathione synthetase, cultured cells of a microorganism producing the mutant glutamate-cysteine ligase and the glutathione synthetase, or a processed product of the cultured cells, wherein the processed product comprises the mutant glutamate-cysteine ligase and the glutathione synthetase.

15. The method according to claim 13, wherein a γ-glutamyltransferase gene is disrupted in the microorganism.

16. The method according to claim 13, wherein the microorganism is *Escherichia coli*.

17. The method according to claim 14, wherein a γ-glutamyltransferase gene is disrupted in the microorganism.

18. The method according to claim 14, wherein the microorganism is *Escherichia coli*.

19. The method according to claim 3, wherein the amino acid residue is mutated in the mutant glutamate-cysteine ligase such that the mutation corresponds to at least one mutation in the amino acid sequence of SEQ ID NO: 2 selected from the group consisting of:

L135I, L135F, L135M, L135V, L135G, L135A, L135W, L135K, L135H, L135R, L135C, L135N, L135S, L135T, Q144F, Q144A, Q144N, Q144S, Q144D, Q144T, Q144R, Q144H, Q144G, Q144K, Q144Y, Q144W, Q144C, Q144M, Q144P, Q144V, Q144L, Q144I, Y241A, N243I, N243W, N243K, N243R, N243H, Y300A, Y300H, Y300R, and Y300K.

20. The method according to claim 3, wherein the amino acid residue is mutated in the mutant glutamate-cysteine ligase such that the mutation corresponds to at least one mutation in the amino acid sequence of SEQ ID NO: 2 selected from the group consisting of:

L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144R/N243F, Q144D/N243W, Q144D/N243F, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, and L135T/Q144L.

21. The method according to claim 3, wherein the amino acid residue is mutated in the mutant glutamate-cysteine ligase such that the mutation corresponds to at least one mutation in the amino acid sequence of SEQ ID NO: 2 selected from the group consisting of:

L135I, L135M, L135V, L135G, L135A, L135K, L135H, L135C, L135N, L135S, L135T, Q144F, Q144A, Q144S, Q144D, Q144T, Q144R, Q144H, Q144K, Q144Y, Q144W, Q144C, Q144M, Q144P, Q144V, Q144L, Q144I, N243R, N243H, Y300R, Y300K, L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144P, L135V/Q144W, L135V/Q144H, L135V/Q144E, L135V/Q144N, L135V/Q144S, L135D/Q144L, L135C/Q144L, L135N/Q144L, L135S/Q144L, and L135T/Q144L.

22. The mutant glutamate cysteine ligase method according to claim 1, wherein a ratio of γ-glutamylvaline synthetase activity of the mutant glutamate-cysteine ligase to γ-glutamylglycine synthetase activity of the mutant glutamate-cysteine ligase is 0.7 or higher.

23. The mutant glutamate cysteine ligase method according to claim 3, wherein a ratio of γ-glutamylvaline synthetase activity of the mutant glutamate-cysteine ligase to γ-glutamylglycine synthetase activity of the mutant glutamate-cysteine ligase is 0.7 or higher.

* * * * *

SEQUENCE LISTING

```
<160> NUMBER OF SEQ ID NOS: 106

<210> SEQ ID NO 1
<211> LENGTH: 1557
<212> TYPE: DNA
<213> ORGANISM: Escherichia coli

<400> SEQUENCE: 1
ttgatcccgg acgtatcaca ggcgctggcc tggctggaaa acatcctca ggcgttaaag      60 gggatacagc gtgggctgga gcgcgaaact ttgcgtgtta atgctgatgg cacactggca     120
acaacaggtc atcctgaagc attaggttcc gcactgacgc acaaatggat tactaccgat     180
tttgcggaag cattgctgga attcattaca ccagtggatg gtgatattga acatatgctg     240
acctttatgc gcgatctgca tcgttatacg gcgcgcaata tgggcgatga gcggatgtgg     300
ccgttaagta tgccatgcta catcgcagaa ggtcaggaca tcgaactggc acagtacggc     360
acttctaaca ccggacgctt taaaacgctg tatcgtgaag ggctgaaaaa tcgctacggc     420
gcgctgatgc aaaccatttc cggcgtgcac tacaatttct ctttgccaat ggcattctgg     480
caagcgaagt gcggtgatat ctcgggcgct gatgccaaag agaaaatttc tgcgggctat     540
ttccgcgtta tccgcaatta ctatcgtttc ggttgggtca ttccttatct gtttggtgca     600
tctccggcga tttgttcttc tttcctgcaa ggaaaaccaa cgtcgctgcc gtttgagaaa     660
accgagtgcg gtatgtatta cctgccgtat gcgacctctc ttcgtttgag cgatctcggc     720
tataccaata aatcgcaaag caatcttggt attaccttca acgatcttta cgagtacgta     780
gcgggcctta acaggcaatc aaaacgcca tcggaagagt acgcgaagat tggtattgag     840
aaagacggta gaggctgca aatcaacagc aacgtgttgc agattgaaaa cgaactgtac     900
gcgccgattc gtccaaaacg cgttacccgc agcggcgagt cgccttctga tgcgctgtta     960
cgtggcggca ttgaatatat tgaagtgcgt tcgctgacaa tcaacccgtt ctcgccgatt    1020
ggtgtagatg aacagcaggt gcgattcctc gacctgttta tggtctggtg tgcgctggct    1080
gatgcaccgg aaatgagcag tagcgaactt gcctgtacac gcgttaactg gaaccgggtg    1140
atcctcgaag gtcgcaaacc gggtctgacg ctgggtatcg gctgcgaaac cgcacagttc    1200
ccgttaccgc aggtgggtaa agatctgttc cgcgatctga aacgcgtcgc gcaaacgctg    1260
gatagtatta acggcggcga agcgtatcag aaagtgtgtg atgaactggt tgcctgcttc    1320
gataatcccg atctgacttt ctctgcccgt atcttaaggt ctatgattga tactggtatt    1380
ggcggaacag gcaaagcatt tgcagaagcc taccgtaatc tgctgcgtga agagccgctg    1440
gaaattctgc gcgaagagga ttttgtagcc gagcgcgagg cgtctgaacg ccgtcagcag    1500
gaaatggaag ccgctgatac cgaaccgttt gcggtgtggc tggaaaaaca cgcctga      1557

<210> SEQ ID NO 2
<211> LENGTH: 518
<212> TYPE: PRT
<213> ORGANISM: Escherichia coli

<400> SEQUENCE: 2

Met Ile Pro Asp Val Ser Gln Ala Leu Ala Trp Leu Glu Lys His Pro
```

-continued

```
  1               5                  10                 15
Gln Ala Leu Lys Gly Ile Gln Arg Gly Leu Glu Arg Glu Thr Leu Arg
                 20                 25                 30

Val Asn Ala Asp Gly Thr Leu Ala Thr Thr Gly His Pro Glu Ala Leu
                 35                 40                 45

Gly Ser Ala Leu Thr His Lys Trp Ile Thr Thr Asp Phe Ala Glu Ala
 50                 55                 60

Leu Leu Glu Phe Ile Thr Pro Val Asp Gly Asp Ile Glu His Met Leu
 65                 70                 75                 80

Thr Phe Met Arg Asp Leu His Arg Tyr Thr Ala Arg Asn Met Gly Asp
                 85                 90                 95

Glu Arg Met Trp Pro Leu Ser Met Pro Cys Tyr Ile Ala Glu Gly Gln
                100                105                110

Asp Ile Glu Leu Ala Gln Tyr Gly Thr Ser Asn Thr Gly Arg Phe Lys
                115                120                125

Thr Leu Tyr Arg Glu Gly Leu Lys Asn Arg Tyr Gly Ala Leu Met Gln
                130                135                140

Thr Ile Ser Gly Val His Tyr Asn Phe Ser Leu Pro Met Ala Phe Trp
145                150                155                160

Gln Ala Lys Cys Gly Asp Ile Ser Gly Ala Asp Ala Lys Glu Lys Ile
                165                170                175

Ser Ala Gly Tyr Phe Arg Val Ile Arg Asn Tyr Tyr Arg Phe Gly Trp
                180                185                190

Val Ile Pro Tyr Leu Phe Gly Ala Ser Pro Ala Ile Cys Ser Ser Phe
                195                200                205

Leu Gln Gly Lys Pro Thr Ser Leu Pro Phe Glu Lys Thr Glu Cys Gly
                210                215                220

Met Tyr Tyr Leu Pro Tyr Ala Thr Ser Leu Arg Leu Ser Asp Leu Gly
225                230                235                240

Tyr Thr Asn Lys Ser Gln Ser Asn Leu Gly Ile Thr Phe Asn Asp Leu
                245                250                255

Tyr Glu Tyr Val Ala Gly Leu Lys Gln Ala Ile Lys Thr Pro Ser Glu
                260                265                270

Glu Tyr Ala Lys Ile Gly Ile Glu Lys Asp Gly Lys Arg Leu Gln Ile
                275                280                285

Asn Ser Asn Val Leu Gln Ile Glu Asn Glu Leu Tyr Ala Pro Ile Arg
                290                295                300

Pro Lys Arg Val Thr Arg Ser Gly Glu Ser Pro Ser Asp Ala Leu Leu
305                310                315                320

Arg Gly Gly Ile Glu Tyr Ile Glu Val Arg Ser Leu Asp Ile Asn Pro
                325                330                335

Phe Ser Pro Ile Gly Val Asp Glu Gln Val Arg Phe Leu Asp Leu
                340                345                350

Phe Met Val Trp Cys Ala Leu Ala Asp Ala Pro Glu Met Ser Ser Ser
                355                360                365

Glu Leu Ala Cys Thr Arg Val Asn Trp Asn Arg Val Ile Leu Glu Gly
                370                375                380

Arg Lys Pro Gly Leu Thr Leu Gly Ile Gly Cys Glu Thr Ala Gln Phe
385                390                395                400

Pro Leu Pro Gln Val Gly Lys Asp Leu Phe Arg Asp Leu Lys Arg Val
                405                410                415

Ala Gln Thr Leu Asp Ser Ile Asn Gly Gly Glu Ala Tyr Gln Lys Val
                420                425                430
```

Cys Asp Glu Leu Val Ala Cys Phe Asp Asn Pro Asp Leu Thr Phe Ser
        435                 440                 445

Ala Arg Ile Leu Arg Ser Met Ile Asp Thr Gly Ile Gly Gly Thr Gly
    450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
            500                 505                 510

Trp Leu Glu Lys His Ala
        515

<210> SEQ ID NO 3
<211> LENGTH: 951
<212> TYPE: DNA
<213> ORGANISM: Escherichia coli

<400> SEQUENCE: 3
atgatcaagc tcggcatcgt gatggacccc atcgcaaaca tcaacatcaa gaaagattcc     60
agttttgcta tgttgctgga agcacagcgt cgtggttacg aacttcacta tatggagatg    120
ggcgatctgt atctgatcaa tggtgaagcc cgcgcccata cccgcacgct gaacgtgaag    180
cagaactacg aagagtggtt ttcgttcgtc ggtgaacagg atctgccgct ggccgatctc    240
gatgtgatcc tgatgcgtaa agacccgccg tttgataccg agtttatcta cgcgacctat    300
attctggaac gtgccgaaga gaaagggacg ctgatcgtta caagccgca gagcctgcgc    360
gactgtaacg agaaactgtt taccgcctgg ttctctgact taacgccaga aacgctggtt    420
acgcgcaata agcgcagct aaaagcgttc tgggagaaac acagcgacat cattcttaag    480
ccgctggacg gtatgggcgg cgcgtcgatt ttccgcgtga agaaggcga tccaaaacctc    540
ggcgtgattg ccgaaacccct gactgagcat ggcactcgct actgcatggc gcaaaattac    600
ctgccagcca ttaaagatgg cgacaaacgt gtgctggtgg tggatggcga ccgtaccg     660
tactgcctgg cgcgtattcc gcaggggggc gaaacccgtg caatctggc tgccggtggt    720
cgcggtgaac ctcgtccgct gacggaaagt gactggaaaa tcgcccgtca gatcgggccg    780
acgctgaaag aaaagggct gattttttgtt ggtctgata tcatcggcga ccgtctgact    840
gaaattaacg tcaccagccc aacctgtatt cgtgagattg aagcagagtt ccggtgtcg    900
atcaccggaa tgttaatgga tgccatcgaa gcacgtttac agcagcagta a            951

<210> SEQ ID NO 4
<211> LENGTH: 316
<212> TYPE: PRT
<213> ORGANISM: Escherichia coli

<400> SEQUENCE: 4

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

| | | | | | | | | | | | | | | | |
|---|---|---|---|---|---|---|---|---|---|---|---|---|---|---|---|
|Glu|Trp|Phe|Ser|Phe|Val|Gly|Glu|Gln|Asp|Leu|Pro|Leu|Ala|Asp|Leu|
|65| | | | |70| | | |75| | | | |80| |

Asp Val Ile Leu Met Arg Lys Asp Pro Pro Phe Asp Thr Glu Phe Ile
            85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
            115                 120                 125

Ala Trp Phe Ser Asp Leu Thr Pro Glu Thr Leu Val Thr Arg Asn Lys
            130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
            165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
            195                 200                 205

Lys Arg Val Leu Val Val Asp Gly Glu Pro Val Pro Tyr Cys Leu Ala
210                 215                 220

Arg Ile Pro Gln Gly Gly Glu Thr Arg Gly Asn Leu Ala Ala Gly Gly
225                 230                 235                 240

Arg Gly Glu Pro Arg Pro Leu Thr Glu Ser Asp Trp Lys Ile Ala Arg
            245                 250                 255

Gln Ile Gly Pro Thr Leu Lys Leu Lys Gly Leu Ile Phe Val Gly Leu
            260                 265                 270

Asp Ile Ile Gly Asp Arg Leu Thr Glu Ile Asn Val Thr Ser Pro Thr
            275                 280                 285

Cys Ile Arg Glu Ile Glu Ala Glu Phe Pro Val Ser Ile Thr Gly Met
            290                 295                 300

Leu Met Asp Ala Ile Glu Ala Arg Leu Gln Gln Gln
305                 310                 315

<210> SEQ ID NO 5
<211> LENGTH: 1743
<212> TYPE: DNA
<213> ORGANISM: Escherichia coli

<400> SEQUENCE: 5

| | | | | |
|---|---|---|---|---|
|atgataaaac cgacgttttt acgccgggtg gccattgctg ctctgctctc aggaagttgt|60|
|tttagcgccg ccgccgcgcc tcctgcgccg cccgtctcgt atggtgtgga ggaagatgtc|120|
|ttccacccgg tacgcgcgaa acagggaatg gtagcgtctg tggacgccac tgccactcag|180|
|gtggggggtgg atattctcaa ggagggcggg aatgccgttg atgccgccgt ggcggtgggc|240|
|tacgcgctgg cggtaacgca tccgcaggca gggaatctgg cggtggtgg ttttatgtta|300|
|atccgctcga aaaatggcaa taccacggct atcgatttcc gcgaaatggc acccgccaaa|360|
|gcgacccgcg atatgttcct cgatgatcag ggcaacccgg acagcaaaaa atcactcact|420|
|tcgcatctgg cttccggcac accgggtacg gtagcaggtt tctcgctggc gctggataaa|480|
|tacggcacca tgccgctgaa caaagtcgtg cagcccgcgt ttaaactggc acgcgatggt|540|
|tttatcgtta acgacgcgct ggctgacgat ctcaaaacct acggtagcga agtgttgccg|600|
|aatcacgaaa acagtaaagc tatcttctgg aaagagggcg agccgctgaa aagggcgac|660|
|acgctggtgc aggcgaacct ggcaaagagc ctggagatga ttgctgaaaa cggcccggac|720|

-continued

```
gaattctata aaggcacgat tgcggaacag atcgcccagg agatgcagaa aaacggtggc      780
ttgatcacta aagaagattt agcagcctat aaagcggtcg aacgcactcc gataagcggc      840
gattatcgcg ggtatcaggt ttactccatg ccaccgccat cctccggcgg gatccatatc      900
gtacaaatcc tcaatattct ggaaaacttc gatatgaaga aatacggctt tggcagcgcc      960
gatgcgatgc aaatcatggc agaagcggag aaatacgcct acgccgaccg ctcggaatat     1020
cttggcgacc cggattttgt caaagtaccg tggcaggcgc tgaccaataa agcctatgcc     1080
aaatctattg ccgatcaaat tgatatcaat aaagcgaagc catccagcga aattcgcccc     1140
ggcaagcttg cgccttatga gagtaatcaa actacccatt actcagtggt ggataaagat     1200
ggtaacgcgg tggcggtgac ctatacgctg aacaccacct tcggtacggg cattgtcgcg     1260
ggcgagagcg gtattctgct taataaccag atggatgatt tctccgccaa accgggcgta     1320
ccgaacgttt acgggctggt gggcggtgat gccaacgccg tcgggccgaa caaacgcccg     1380
ctgtcgtcga tgtcgccgac cattgtggtg aaagacggta aaacctggct ggttaccggt     1440
agcccaggcg gtagccggat catcactaca gtgctgcaaa tggtggtgaa tagcatcgat     1500
tatggcttga acgtcgccga agcgaccaat gcgccgcgtt tccaccatca gtggttgccg     1560
gacgagctgc gtgtcgaaaa agggtttagc ccggatacgc tcaagctgct ggaagcaaaa     1620
ggtcagaaag tggcgctgaa agaggcgatg ggcagtacac aaagcattat ggtttgggccg     1680 gacggtgagt tgtacggcgc atccgacccg cgctcggtgg atgatttaac ggcggggtac     1740
taa                                                                  1743
```

<210> SEQ ID NO 6
<211> LENGTH: 580
<212> TYPE: PRT
<213> ORGANISM: Escherichia coli

<400> SEQUENCE: 6

```
Met Ile Lys Pro Thr Phe Leu Arg Arg Val Ala Ile Ala Ala Leu Leu
1               5                  10                  15

Ser Gly Ser Cys Phe Ser Ala Ala Ala Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Thr Gln Val Gly Val Asp
    50                  55                  60

Ile Leu Lys Glu Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Asp Leu Lys
```

```
            180                 185                 190
Thr Tyr Gly Ser Glu Val Leu Pro Asn His Glu Asn Ser Lys Ala Ile
            195                 200                 205

Phe Trp Lys Glu Gly Glu Pro Leu Lys Lys Gly Asp Thr Leu Val Gln
            210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
                260                 265                 270

Val Glu Arg Thr Pro Ile Ser Gly Asp Tyr Arg Gly Tyr Gln Val Tyr
            275                 280                 285

Ser Met Pro Pro Pro Ser Ser Gly Gly Ile His Ile Val Gln Ile Leu
            290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
                340                 345                 350

Ala Leu Thr Asn Lys Ala Tyr Ala Lys Ser Ile Ala Asp Gln Ile Asp
                355                 360                 365

Ile Asn Lys Ala Lys Pro Ser Ser Glu Ile Arg Pro Gly Lys Leu Ala
            370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Leu Asn Asn Gln Met Asp
            420                 425                 430

Asp Phe Ser Ala Lys Pro Gly Val Pro Asn Val Tyr Gly Leu Val Gly
            435                 440                 445

Gly Asp Ala Asn Ala Val Gly Pro Asn Lys Arg Pro Leu Ser Ser Met
            450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
            515                 520                 525

Phe Ser Pro Asp Thr Leu Lys Leu Leu Glu Ala Lys Gly Gln Lys Val
            530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
            580

<210> SEQ ID NO 7
```

```
<211> LENGTH: 30
<212> TYPE: DNA
<213> ORGANISM: Artificial Sequence
<220> FEATURE:
<223> OTHER INFORMATION: primer

<400> SEQUENCE: 7
gggcgatcgc cattgcgtaa aacatcgcgc                                    30

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gggaactgca ggcgcttcca tc                                            22

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gggaagcttc agcagtggca gaag                                          24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gggggatcct ggagagcagg catg                                          24

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ggcatactta acggcagcat ccgctcatcg cc                                 32

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
ggcgatgagc ggatgctgcc gttaagtatg cc                                 32

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
```
gatacgtccg ggatcatatt gacctcccgc c                                    31

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
ggcgggaggt caatatgatc ccggacgtat c                                    31

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
gacgctttaa aacgctgtat cttgaagggc tgaaaaatgc                           40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
cgattttcca gcccttcaag atacagcgtt ttaaagcgtc                           40

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
gacgctttaa aacgctgtat gttgaagggc tgaaaaatgc                           40

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
cgattttcca gcccttcaac atacagcgtt ttaaagcgtc                           40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
gacgctttaa aacgctgtat tttgaagggc tgaaaaatgc                           40

<210> SEQ ID NO 20
<211> LENGTH: 40
<212> TYPE: DNA

<213> ORGANISM: Artificial Sequence
<220> FEATURE:
<223> OTHER INFORMATION: primer

<400> SEQUENCE: 20 cgattttca gcccttcaaa atacagcgtt ttaaagcgtc         40

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21
gacgctttaa aacgctgtat gctgaagggc tgaaaaatgc         40

<210> SEQ ID NO 22
<211> LENGTH: 40
<212> TYPE: DNA
<213> ORGANISM: Artificial Sequence
<220> FEATURE:
<223> OTHER INFORMATION: primer

<400> SEQUENCE: 22 cgattttca gcccttcagc atacagcgtt ttaaagcgtc         40

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
ctacggcgcg ctgatgttta ccatttccgg cgtgcactac         40

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
gtagtgcacg ccggaaatgg taaacatcag cgcgccgtag         40

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
ctacggcgcg ctgatggcaa ccatttccgg cgtgcactac         40

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
gtagtgcacg ccggaaatgg ttgccatcag cgcgccgtag         40

<210> SEQ ID NO 27
<211> LENGTH: 34
<212> TYPE: DNA
<213> ORGANISM: Artificial Sequence
<220> FEATURE:
<223> OTHER INFORMATION: primer

<400> SEQUENCE: 27
aaggaggaat ccataatgat cccggacgta tcac        34

<210> SEQ ID NO 28
<211> LENGTH: 71
<212> TYPE: DNA
<213> ORGANISM: Artificial Sequence
<220> FEATURE:
<223> OTHER INFORMATION: primer

<400> SEQUENCE: 28
ccaagcttgc atgcctcaat gatgatgatg atgatgggcg tgttttttcca gccacaccgc        60 aaacggttcg g        71

<210> SEQ ID NO 29
<211> LENGTH: 33
<212> TYPE: DNA
<213> ORGANISM: Artificial Sequence
<220> FEATURE:
<223> OTHER INFORMATION: primer

<400> SEQUENCE: 29
ctgtatcgtg aagggattaa aaatcgctac ggc        33

<210> SEQ ID NO 30
<211> LENGTH: 33
<212> TYPE: DNA
<213> ORGANISM: Artificial Sequence
<220> FEATURE:
<223> OTHER INFORMATION: primer

<400> SEQUENCE: 30
gccgtagcga tttttaatcc cttcacgata cag        33

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
ctgtatcgtg aagggtttaa aaatcgctac ggc        33

<210> SEQ ID NO 32
<211> LENGTH: 33
<212> TYPE: DNA
<213> ORGANISM: Artificial Sequence
<220> FEATURE:
<223> OTHER INFORMATION: primer

<400> SEQUENCE: 32
gccgtagcga tttttaaacc cttcacgata cag        33

<210> SEQ ID NO 33
<211> LENGTH: 33
<212> TYPE: DNA

```
<213> ORGANISM: Artificial Sequence
<220> FEATURE:
<223> OTHER INFORMATION: primer

<400> SEQUENCE: 33
ctgtatcgtg aagggatgaa aaatcgctac ggc                              33

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
gccgtagcga tttttcatcc cttcacgata cag                              33

<210> SEQ ID NO 35
<211> LENGTH: 33
<212> TYPE: DNA
<213> ORGANISM: Artificial Sequence
<220> FEATURE:
<223> OTHER INFORMATION: primer

<400> SEQUENCE: 35
ctgtatcgtg aagggtgaa aaatcgctac ggc                               33

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
gccgtagcga tttttcaccc cttcacgata cag                              33

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
ctgtatcgtg aaggggcaa aaatcgctac ggc                               33

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
gccgtagcga tttttgcccc cttcacgata cag                              33

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
ctgtatcgtg aagggcgaa aaatcgctac ggc                               33
```

<210> SEQ ID NO 40
<211> LENGTH: 33
<212> TYPE: DNA
<213> ORGANISM: Artificial Sequence
<220> FEATURE:
<223> OTHER INFORMATION: primer

<400> SEQUENCE: 40
gccgtagcga ttttcgccc cttcacgata cag                         33

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
ctgtatcgtg aagggtggaa aaatcgctac ggc                         33

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
gccgtagcga ttttccacc cttcacgata cag                         33

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
ctgtatcgtg aagggaaaaa aaatcgctac ggc                         33

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
gccgtagcga ttttttttcc cttcacgata cag                         33

<210> SEQ ID NO 45
<211> LENGTH: 33
<212> TYPE: DNA
<213> ORGANISM: Artificial Sequence
<220> FEATURE:
<223> OTHER INFORMATION: primer

<400> SEQUENCE: 45
ctgtatcgtg aagggcataa aaatcgctac ggc                         33

<210> SEQ ID NO 46
<211> LENGTH: 33
<212> TYPE: DNA
<213> ORGANISM: Artificial Sequence
<220> FEATURE:

<223> OTHER INFORMATION: primer

<400> SEQUENCE: 46
gccgtagcga tttttatgcc cttcacgata cag                           33

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
gctacggcgc gctgatgttc accatttccg gcgtg                         35

<210> SEQ ID NO 48
<211> LENGTH: 35
<212> TYPE: DNA
<213> ORGANISM: Artificial Sequence
<220> FEATURE:
<223> OTHER INFORMATION: primer

<400> SEQUENCE: 48
cacgccggaa atggtgaaca tcagcgcgcc gtagc                         35

<210> SEQ ID NO 49
<211> LENGTH: 34
<212> TYPE: DNA
<213> ORGANISM: Artificial Sequence
<220> FEATURE:
<223> OTHER INFORMATION: primer

<400> SEQUENCE: 49
ctacggcgcg ctgatggcga ccatttccgg cgtg                          34

<210> SEQ ID NO 50
<211> LENGTH: 34
<212> TYPE: DNA
<213> ORGANISM: Artificial Sequence
<220> FEATURE:
<223> OTHER INFORMATION: primer

<400> SEQUENCE: 50
cacgccggaa atggtcgcca tcagcgcgcc gtag                          34

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
gctacggcgc gctgatgaac accatttccg gcgtg                         35

<210> SEQ ID NO 52
<211> LENGTH: 35
<212> TYPE: DNA
<213> ORGANISM: Artificial Sequence
<220> FEATURE:
<223> OTHER INFORMATION: primer

<400> SEQUENCE: 52
cacgccggaa atggtgttca tcagcgcgcc gtagc                         35

```
<210> SEQ ID NO 53
<211> LENGTH: 35
<212> TYPE: DNA
<213> ORGANISM: Artificial Sequence
<220> FEATURE:
<223> OTHER INFORMATION: primer

<400> SEQUENCE: 53
gctacggcgc gctgatgtcg accatttccg gcgtg                              35

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
cacgccggaa atggtcgaca tcagcgcgcc gtagc                              35

<210> SEQ ID NO 55
<211> LENGTH: 35
<212> TYPE: DNA
<213> ORGANISM: Artificial Sequence
<220> FEATURE:
<223> OTHER INFORMATION: primer

<400> SEQUENCE: 55
gctacggcgc gctgatggat accatttccg gcgtg                              35

<210> SEQ ID NO 56
<211> LENGTH: 35
<212> TYPE: DNA
<213> ORGANISM: Artificial Sequence
<220> FEATURE:
<223> OTHER INFORMATION: primer

<400> SEQUENCE: 56
cacgccggaa atggtatcca tcagcgcgcc gtagc                              35

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
gctacggcgc gctgatgacc accatttccg gcgtg                              35

<210> SEQ ID NO 58
<211> LENGTH: 35
<212> TYPE: DNA
<213> ORGANISM: Artificial Sequence
<220> FEATURE:
<223> OTHER INFORMATION: primer

<400> SEQUENCE: 58
cacgccggaa atggtggtca tcagcgcgcc gtagc                              35

<210> SEQ ID NO 59
<211> LENGTH: 35
<212> TYPE: DNA
<213> ORGANISM: Artificial Sequence
<220> FEATURE:
<223> OTHER INFORMATION: primer
```

```
<400> SEQUENCE: 59
gctacggcgc gctgatgcgc accatttccg gcgtg          35

<210> SEQ ID NO 60
<211> LENGTH: 35
<212> TYPE: DNA
<213> ORGANISM: Artificial Sequence
<220> FEATURE:
<223> OTHER INFORMATION: primer

<400> SEQUENCE: 60
cacgccggaa atggtgcgca tcagcgcgcc gtagc          35

<210> SEQ ID NO 61
<211> LENGTH: 35
<212> TYPE: DNA
<213> ORGANISM: Artificial Sequence
<220> FEATURE:
<223> OTHER INFORMATION: primer

<400> SEQUENCE: 61
gctacggcgc gctgatgcat accatttccg gcgtg          35

<210> SEQ ID NO 62
<211> LENGTH: 35
<212> TYPE: DNA
<213> ORGANISM: Artificial Sequence
<220> FEATURE:
<223> OTHER INFORMATION: primer

<400> SEQUENCE: 62
cacgccggaa atggtatgca tcagcgcgcc gtagc          35

<210> SEQ ID NO 63
<211> LENGTH: 35
<212> TYPE: DNA
<213> ORGANISM: Artificial Sequence
<220> FEATURE:
<223> OTHER INFORMATION: primer

<400> SEQUENCE: 63
gctacggcgc gctgatgggc accatttccg gcgtg          35

<210> SEQ ID NO 64
<211> LENGTH: 35
<212> TYPE: DNA
<213> ORGANISM: Artificial Sequence
<220> FEATURE:
<223> OTHER INFORMATION: primer

<400> SEQUENCE: 64
cacgccggaa atggtgccca tcagcgcgcc gtagc          35

<210> SEQ ID NO 65
<211> LENGTH: 35
<212> TYPE: DNA
<213> ORGANISM: Artificial Sequence
<220> FEATURE:
<223> OTHER INFORMATION: primer

<400> SEQUENCE: 65
gctacggcgc gctgatgaaa accatttccg gcgtg          35

<210> SEQ ID NO 66
<211> LENGTH: 35
```

```
<212> TYPE: DNA
<213> ORGANISM: Artificial Sequence
<220> FEATURE:
<223> OTHER INFORMATION: primer

<400> SEQUENCE: 66
cacgccggaa atggttttca tcagcgcgcc gtagc                            35

<210> SEQ ID NO 67
<211> LENGTH: 35
<212> TYPE: DNA
<213> ORGANISM: Artificial Sequence
<220> FEATURE:
<223> OTHER INFORMATION: primer

<400> SEQUENCE: 67
gctacggcgc gctgatgtat accatttccg gcgtg                            35

<210> SEQ ID NO 68
<211> LENGTH: 35
<212> TYPE: DNA
<213> ORGANISM: Artificial Sequence
<220> FEATURE:
<223> OTHER INFORMATION: primer

<400> SEQUENCE: 68
cacgccggaa atggtataca tcagcgcgcc gtagc                            35

<210> SEQ ID NO 69
<211> LENGTH: 35
<212> TYPE: DNA
<213> ORGANISM: Artificial Sequence
<220> FEATURE:
<223> OTHER INFORMATION: primer

<400> SEQUENCE: 69
gctacggcgc gctgatgtgg accatttccg gcgtg                            35

<210> SEQ ID NO 70
<211> LENGTH: 35
<212> TYPE: DNA
<213> ORGANISM: Artificial Sequence
<220> FEATURE:
<223> OTHER INFORMATION: primer

<400> SEQUENCE: 70
cacgccggaa atggtccaca tcagcgcgcc gtagc                            35

<210> SEQ ID NO 71
<211> LENGTH: 35
<212> TYPE: DNA
<213> ORGANISM: Artificial Sequence
<220> FEATURE:
<223> OTHER INFORMATION: primer

<400> SEQUENCE: 71
gctacggcgc gctgatgtgc accatttccg gcgtg                            35

<210> SEQ ID NO 72
<211> LENGTH: 35
<212> TYPE: DNA
<213> ORGANISM: Artificial Sequence
<220> FEATURE:
<223> OTHER INFORMATION: primer

<400> SEQUENCE: 72
```
cacgccggaa atggtgcaca tcagcgcgcc gtagc        35

<210> SEQ ID NO 73
<211> LENGTH: 35
<212> TYPE: DNA
<213> ORGANISM: Artificial Sequence
<220> FEATURE:
<223> OTHER INFORMATION: primer

<400> SEQUENCE: 73
gctacggcgc gctgatgatg accatttccg gcgtg        35

<210> SEQ ID NO 74
<211> LENGTH: 35
<212> TYPE: DNA
<213> ORGANISM: Artificial Sequence
<220> FEATURE:
<223> OTHER INFORMATION: primer

<400> SEQUENCE: 74
cacgccggaa atggtcatca tcagcgcgcc gtagc        35

<210> SEQ ID NO 75
<211> LENGTH: 35
<212> TYPE: DNA
<213> ORGANISM: Artificial Sequence
<220> FEATURE:
<223> OTHER INFORMATION: primer

<400> SEQUENCE: 75
gctacggcgc gctgatgccg accatttccg gcgtg        35

<210> SEQ ID NO 76
<211> LENGTH: 35
<212> TYPE: DNA
<213> ORGANISM: Artificial Sequence
<220> FEATURE:
<223> OTHER INFORMATION: primer

<400> SEQUENCE: 76
cacgccggaa atggtcggca tcagcgcgcc gtagc        35

<210> SEQ ID NO 77
<211> LENGTH: 35
<212> TYPE: DNA
<213> ORGANISM: Artificial Sequence
<220> FEATURE:
<223> OTHER INFORMATION: primer

<400> SEQUENCE: 77
gctacggcgc gctgatggtg accatttccg gcgtg        35

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
cacgccggaa atggtcacca tcagcgcgcc gtagc        35

<210> SEQ ID NO 79
<211> LENGTH: 35
<212> TYPE: DNA
<213> ORGANISM: Artificial Sequence

```
<220> FEATURE:
<223> OTHER INFORMATION: primer

<400> SEQUENCE: 79
gctacggcgc gctgatgctg accatttccg gcgtg                              35

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
cacgccggaa atggtcagca tcagcgcgcc gtagc                              35

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
gctacggcgc gctgatgatt accatttccg gcgtg                              35

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
cacgccggaa atggtaatca tcagcgcgcc gtagc                              35

<210> SEQ ID NO 83
<211> LENGTH: 33
<212> TYPE: DNA
<213> ORGANISM: Artificial Sequence
<220> FEATURE:
<223> OTHER INFORMATION: primer

<400> SEQUENCE: 83
ttgagcgatc tcggcgcgac caataaatcg caa                                33

<210> SEQ ID NO 84
<211> LENGTH: 33
<212> TYPE: DNA
<213> ORGANISM: Artificial Sequence
<220> FEATURE:
<223> OTHER INFORMATION: primer

<400> SEQUENCE: 84
ttgcgattta ttggtcgcgc cgagatcgct caa                                33

<210> SEQ ID NO 85
<211> LENGTH: 34
<212> TYPE: DNA
<213> ORGANISM: Artificial Sequence
<220> FEATURE:
<223> OTHER INFORMATION: primer

<400> SEQUENCE: 85
gatctcggct ataccattaa atcgcaaagc aatc                               34
```

<210> SEQ ID NO 86
<211> LENGTH: 34
<212> TYPE: DNA
<213> ORGANISM: Artificial Sequence
<220> FEATURE:
<223> OTHER INFORMATION: primer

<400> SEQUENCE: 86
gattgctttg cgatttaatg gtatagccga gatc                          34

<210> SEQ ID NO 87
<211> LENGTH: 34
<212> TYPE: DNA
<213> ORGANISM: Artificial Sequence
<220> FEATURE:
<223> OTHER INFORMATION: primer

<400> SEQUENCE: 87
gatctcggct atacctttaa atcgcaaagc aatc                          34

<210> SEQ ID NO 88
<211> LENGTH: 34
<212> TYPE: DNA
<213> ORGANISM: Artificial Sequence
<220> FEATURE:
<223> OTHER INFORMATION: primer

<400> SEQUENCE: 88
gattgctttg cgatttaaag gtatagccga gatc                          34

<210> SEQ ID NO 89
<211> LENGTH: 34
<212> TYPE: DNA
<213> ORGANISM: Artificial Sequence
<220> FEATURE:
<223> OTHER INFORMATION: primer

<400> SEQUENCE: 89
gatctcggct atacctggaa atcgcaaagc aatc                          34

<210> SEQ ID NO 90
<211> LENGTH: 34
<212> TYPE: DNA
<213> ORGANISM: Artificial Sequence
<220> FEATURE:
<223> OTHER INFORMATION: primer

<400> SEQUENCE: 90
gattgctttg cgatttccag gtatagccga gatc                          34

<210> SEQ ID NO 91
<211> LENGTH: 33
<212> TYPE: DNA
<213> ORGANISM: Artificial Sequence
<220> FEATURE:
<223> OTHER INFORMATION: primer

<400> SEQUENCE: 91
gatctcggct ataccccgaa atcgcaaagc aat                           33

<210> SEQ ID NO 92
<211> LENGTH: 33
<212> TYPE: DNA
<213> ORGANISM: Artificial Sequence
<220> FEATURE:
<223> OTHER INFORMATION: primer

<400> SEQUENCE: 92
attgctttgc gatttcgggg tatagccgag atc                                    33

<210> SEQ ID NO 93
<211> LENGTH: 33
<212> TYPE: DNA
<213> ORGANISM: Artificial Sequence
<220> FEATURE:
<223> OTHER INFORMATION: primer

<400> SEQUENCE: 93
gatctcggct atacctataa atcgcaaagc aat                                    33

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
attgctttgc gatttatagg tatagccgag atc                                    33

<210> SEQ ID NO 95
<211> LENGTH: 33
<212> TYPE: DNA
<213> ORGANISM: Artificial Sequence
<220> FEATURE:
<223> OTHER INFORMATION: primer

<400> SEQUENCE: 95
gatctcggct atacccgcaa atcgcaaagc aat                                    33

<210> SEQ ID NO 96
<211> LENGTH: 33
<212> TYPE: DNA
<213> ORGANISM: Artificial Sequence
<220> FEATURE:
<223> OTHER INFORMATION: primer

<400> SEQUENCE: 96
attgctttgc gatttgcggg tatagccgag atc                                    33

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97
gatctcggct atacctgcaa atcgcaaagc aat                                    33

<210> SEQ ID NO 98
<211> LENGTH: 33
<212> TYPE: DNA
<213> ORGANISM: Artificial Sequence
<220> FEATURE:
<223> OTHER INFORMATION: primer

<400> SEQUENCE: 98
attgctttgc gatttgcagg tatagccgag atc                                    33

<210> SEQ ID NO 99

```
<211> LENGTH: 33
<212> TYPE: DNA
<213> ORGANISM: Artificial Sequence
<220> FEATURE:
<223> OTHER INFORMATION: primer

<400> SEQUENCE: 99
attgaaaacg aactggcggc gccgattcgt cca                          33

<210> SEQ ID NO 100
<211> LENGTH: 33
<212> TYPE: DNA
<213> ORGANISM: Artificial Sequence
<220> FEATURE:
<223> OTHER INFORMATION: primer

<400> SEQUENCE: 100
tggacgaatc ggcgccgcca gttcgttttc aat                          33

<210> SEQ ID NO 101
<211> LENGTH: 33
<212> TYPE: DNA
<213> ORGANISM: Artificial Sequence
<220> FEATURE:
<223> OTHER INFORMATION: primer

<400> SEQUENCE: 101
attgaaaacg aactgcatgc gccgattcgt cca                          33

<210> SEQ ID NO 102
<211> LENGTH: 33
<212> TYPE: DNA
<213> ORGANISM: Artificial Sequence
<220> FEATURE:
<223> OTHER INFORMATION: primer

<400> SEQUENCE: 102
tggacgaatc ggcgcatgca gttcgttttc aat                          33

<210> SEQ ID NO 103
<211> LENGTH: 33
<212> TYPE: DNA
<213> ORGANISM: Artificial Sequence
<220> FEATURE:
<223> OTHER INFORMATION: primer

<400> SEQUENCE: 103
attgaaaacg aactgcgcgc gccgattcgt cca                          33

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104
tggacgaatc ggcgcgcgca gttcgttttc aat                          33

<210> SEQ ID NO 105
<211> LENGTH: 33
<212> TYPE: DNA
<213> ORGANISM: Artificial Sequence
<220> FEATURE:
<223> OTHER INFORMATION: primer

<400> SEQUENCE: 105
```

```
attgaaaacg aactgaaagc gccgattcgt cca                              33

<210> SEQ ID NO 106
<211> LENGTH: 33
<212> TYPE: DNA
<213> ORGANISM: Artificial Sequence
<220> FEATURE:
<223> OTHER INFORMATION: primer

<400> SEQUENCE: 106
tggacgaatc ggcgctttca gttcgttttc aat                              33
```